(12) United States Patent
Shibayama et al.

(10) Patent No.: US 9,588,049 B2
(45) Date of Patent: Mar. 7, 2017

(54) SURFACE-ENHANCED RAMAN SCATTERING UNIT, AND METHOD FOR USING SAME

(71) Applicant: HAMAMATSU PHOTONICS K.K., Hamamatsu-shi, Shizuoka (JP)

(72) Inventors: Katsumi Shibayama, Hamamatsu (JP); Masashi Ito, Hamamatsu (JP); Takafumi Yokino, Hamamatsu (JP); Masaki Hirose, Hamamatsu (JP); Anna Yoshida, Hamamatsu (JP); Kazuto Ofuji, Hamamatsu (JP); Yoshihiro Maruyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 123 days.

(21) Appl. No.: 14/420,441

(22) PCT Filed: Aug. 9, 2013

(86) PCT No.: PCT/JP2013/071702
§ 371 (c)(1),
(2) Date: Feb. 9, 2015

(87) PCT Pub. No.: WO2014/025033
PCT Pub. Date: Feb. 13, 2014

(65) Prior Publication Data
US 2015/0204792 A1  Jul. 23, 2015

(30) Foreign Application Priority Data

Aug. 10, 2012  (JP) .................................. 2012-178766

(51) Int. Cl.
*G01J 3/44* (2006.01)
*G01N 21/65* (2006.01)
(Continued)

(52) U.S. Cl.
CPC .............. *G01N 21/658* (2013.01); *G01J 3/12* (2013.01); *B82Y 40/00* (2013.01); *G01N 2201/02* (2013.01); *G01N 2201/06113* (2013.01)

(58) Field of Classification Search
CPC ............... G01N 21/658; G01N 220/02; G01N 2201/06113; G01N 21/65; G01N 2021/656; G01J 3/44; G01J 3/02
See application file for complete search history.

(56) References Cited

U.S. PATENT DOCUMENTS 5,655,661 A    8/1997  Rigby
7,545,490 B1   6/2009  Pendell-Jones
(Continued)

FOREIGN PATENT DOCUMENTS

CN    1563989    1/2005
CN    1957245    5/2007
(Continued)

OTHER PUBLICATIONS

K. Nakamoto et al., "Arrays of Metallic Nanopillars in Holes for Plasmonic Devices", Retrieved from the Internet: URL: http://www.rsc.org/images/LOC/2011/PDFs/Papers/596_0021.pdf, Oct. 6, 2011, XP055289892.
(Continued)

*Primary Examiner* — Abdullahi Nur
(74) *Attorney, Agent, or Firm* — Drinker Biddle & Reath LLP

(57) ABSTRACT

A SERS unit comprises a substrate; an optical function part formed on the substrate, for generating surface-enhanced Raman scattering; and a package containing the optical function part in an inert space and configured to irreversibly expose the space.

7 Claims, 37 Drawing Sheets

(51) Int. Cl.
*G01J 3/12* (2006.01)
*B82Y 40/00* (2011.01)

(56) References Cited

U.S. PATENT DOCUMENTS

| | | | |
|---|---|---|---|
| 2004/0023046 A1 | 2/2004 | Schlottig et al. | |
| 2006/0034729 A1 | 2/2006 | Poponin | |
| 2006/0146323 A1 | 7/2006 | Bratkovski et al. | |
| 2006/0164637 A1 | 7/2006 | Wang | |
| 2007/0140900 A1* | 6/2007 | Wang .................. | G01J 3/44 422/400 |
| 2007/0254377 A1 | 11/2007 | Li et al. | |
| 2008/0094621 A1 | 4/2008 | Li et al. | |
| 2008/0174775 A1 | 7/2008 | Moskovits et al. | |
| 2008/0218761 A1 | 9/2008 | Nishikawa et al. | |
| 2009/0137411 A1 | 5/2009 | Sun et al. | |
| 2010/0009456 A1 | 1/2010 | Prins et al. | |
| 2010/0321684 A1 | 12/2010 | Bratkovski et al. | |
| 2011/0027901 A1 | 2/2011 | Gaster et al. | |
| 2011/0116089 A1 | 5/2011 | Schmidt et al. | |
| 2011/0166045 A1 | 7/2011 | Dhawan et al. | |
| 2011/0194116 A1 | 8/2011 | Horiuchi et al. | |
| 2012/0265038 A1 | 10/2012 | Kawamura et al. | |
| 2015/0204792 A1 | 7/2015 | Shibayama et al. | |

FOREIGN PATENT DOCUMENTS

| | | |
|---|---|---|
| CN | 101281133 | 10/2008 |
| CN | 101319994 | 12/2008 |
| CN | 101523212 | 9/2009 |
| CN | 102590088 | 9/2009 |
| CN | 101936906 | 1/2011 |
| CN | 102282094 | 12/2011 |
| CN | 102483354 | 5/2012 |
| CN | 103930780 | 7/2014 |
| CN | 104011520 | 8/2014 |
| EP | 2101166 | 9/2009 |
| JP | H05-044867 U | 6/1993 |
| JP | H07-260646 A | 10/1995 |
| JP | 2003-026232 A | 1/2003 |
| JP | 2005-337771 A | 12/2005 |
| JP | 2007-530925 A | 11/2007 |
| JP | 2007-538264 A | 12/2007 |
| JP | 2008-519254 A | 6/2008 |
| JP | 2008-196992 A | 8/2008 |
| JP | 2008-268059 A | 11/2008 |
| JP | 2009-025316 A | 2/2009 |
| JP | 2009-047623 A | 3/2009 |
| JP | 2009-103643 A | 5/2009 |
| JP | 2009-222507 A | 10/2009 |
| JP | 2009-236830 A | 10/2009 |
| JP | 2009-544967 A | 12/2009 |
| JP | 2010-506191 A | 2/2010 |
| JP | 2011-021085 | 2/2011 |
| JP | 2011-033518 A | 2/2011 |
| JP | 2011-506916 A | 3/2011 |
| JP | 2011-075348 A | 4/2011 |
| JP | 2011-107032 A | 6/2011 |
| JP | 2011-141265 A | 7/2011 |
| JP | 2011-215021 A | 10/2011 |
| JP | 2012-233707 A | 11/2012 |
| WO | WO-2007/149120 A2 | 12/2007 |
| WO | WO-2010/050203 A1 | 5/2010 |
| WO | WO-2010/090111 A1 | 8/2010 |
| WO | WO-2011/021085 A2 | 2/2011 |
| WO | WO-2011/040504 A1 | 4/2011 |
| WO | WO 2011/047199 | 4/2011 |
| WO | WO-2012/024006 A2 | 2/2012 |
| WO | WO 2013/015810 | 1/2013 |
| WO | WO 2013/058739 | 4/2013 |
| WO | WO 2013/062540 | 5/2013 |
| WO | WO-2014/025033 A1 | 2/2014 |
| WO | WO-2014/025034 A1 | 2/2014 |

OTHER PUBLICATIONS

M. Tomohiko et al., "New localized surface plasmon resonance sensor utilizing nanoimprinting technology", NSTI Nanotechnology Conference and Trade Show-NSTI Nanotech, vol. 1, May 11, 2006, p. 58-p. 61, XP009098538.

W. D. Li et al., "Three-dimensional cavity nanoantenna coupled plasmonic nanodots for ultrahigh and uniform surface-enhanced Raman scattering over large area", Optics Express, vol. 19, No. 5, Feb. 14, 2011, pp. 3925-3936, XP002751299.

"Q-SERS™ G1 Substrate," Opto Science, Inc. (retrieved on-line on Jul. 5, 2013).

Masahiro Yanagisawa, "Detection of Trace Organic Gas Using Molecular Sensor with Plasmon Antenna," Green Technology, Vo. 22, No. 6, Jun. 10, 2012, pp. 42-47, including at least partial English-language translation.

U.S. Office Action dated Oct. 19, 2015 that issued in U.S. Appl. No. 14/420,483 including a Double Patenting Rejection on pp. 13-15.

W. Zhang et al, "Giant and uniform fluorescence enhancement over large area using plamonic nanodots in 3D resonant cavity nanoantetma by nanoimprinting", Nanotechnolgy, vol. 23, No, 22, May 10, 2012, p. 225301, XP020224099.

S. M. Wells et al, "Efficient disc on pillar substrates for surface enhanced Raman spectroscopy", Chemical Communications—Chemcom, vol. 47, No. 13, Jan. 1, 2011, pp. 3814-3816, XP055289549.

U.S. Office Action dated Oct. 14, 2016 that issued in U.S. Appl. No. 14/420,510 including Double Patenting Rejections on pp. 2-14.

English Machine Translation of JP 2011-107032, Nishikawa et al., Jun. 2, 2011 as attached to U.S. Office Action dated Oct. 14, 2016 in U.S. Appl. No. 14/420,510.

* cited by examiner

Fig.32
(a)
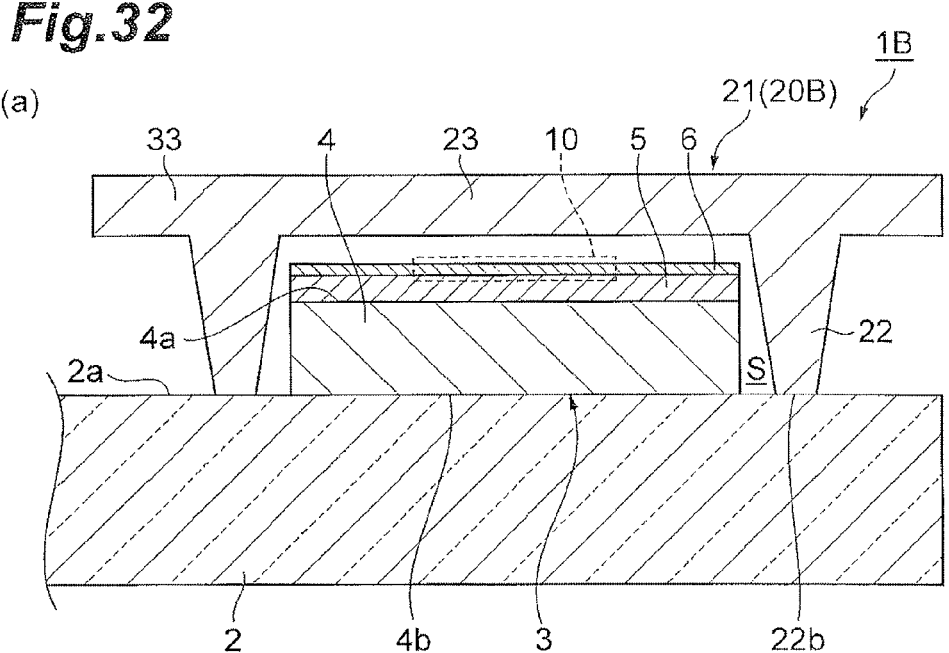
(b)
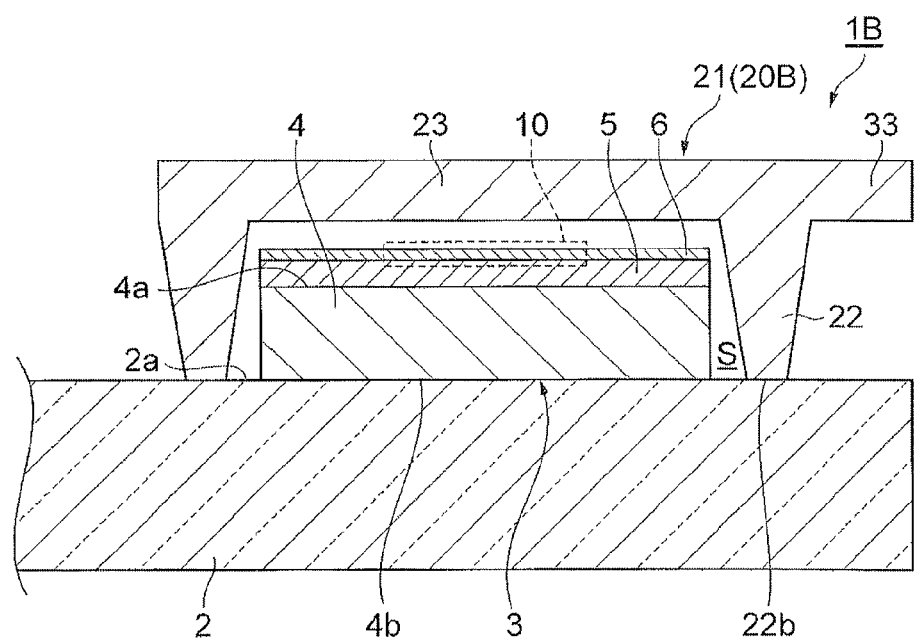

50nm

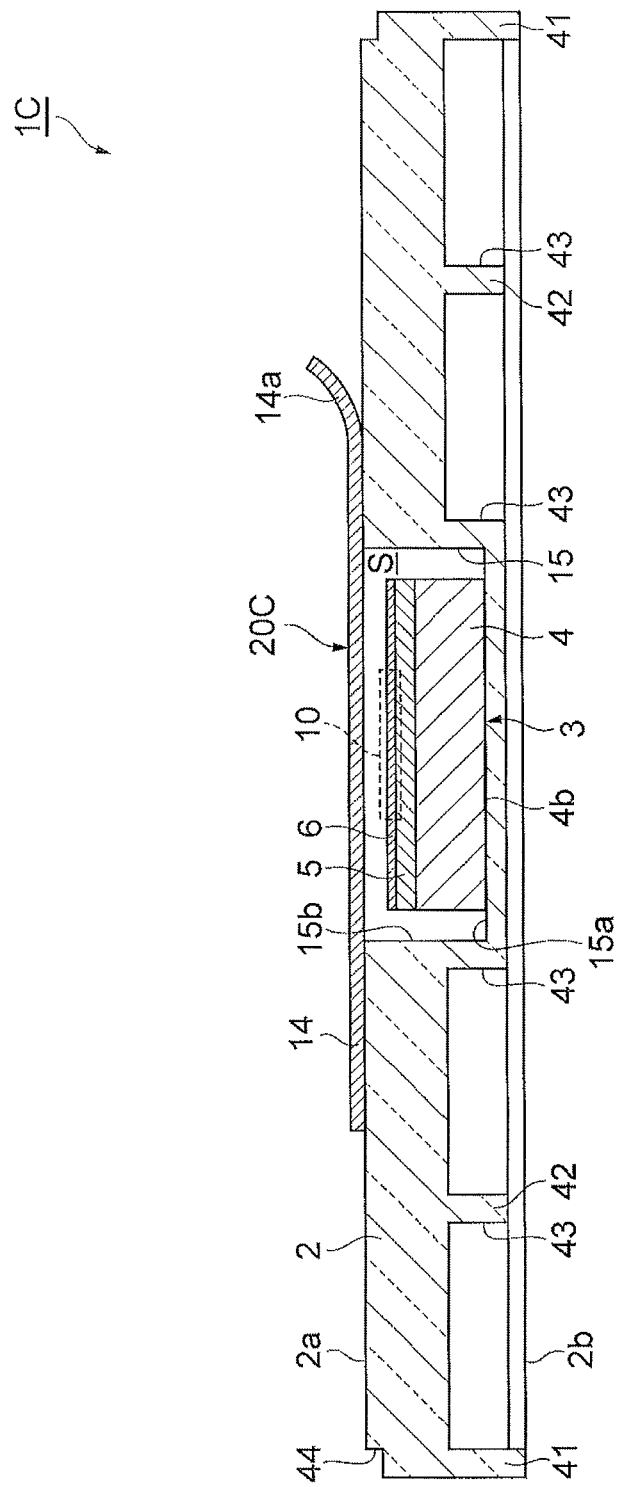

SURFACE-ENHANCED RAMAN SCATTERING UNIT, AND METHOD FOR USING SAME

TECHNICAL FIELD

The present invention relates to a surface-enhanced Raman scattering unit and a method for using the same.

BACKGROUND ART

As a conventional surface-enhanced Raman scattering unit, one equipped with a minute metal structure for generate surface-enhanced Raman scattering (SERS) has been known (see, for example, Patent Literature 1 and Non Patent Literature 1). In such a surface-enhanced Raman scattering unit, when a sample to be subjected to Raman spectroscopy is brought into contact with the minute metal structure and is irradiated with excitation light in this state, surface-enhanced Raman scattering occurs, whereby Raman scattering light enhanced by about $10^8$ times, for example, is released.

CITATION LIST

Patent Literature

Patent Literature 1: Japanese Patent Application Laid-Open No. 2011-33518

Non Patent Literature

Non Patent Literature 1: "Q-SERS™ G1 Substrate", [online], Opto Science, Inc., [retrieved on Jul. 19, 2012]. Retrieved from the Internet:<URL: http://www.optoscience.com/maker/nanova/pdf/Q-SERS_G1.pdf>.

SUMMARY OF INVENTION

Technical Problem

However, the above-mentioned surface-enhanced Raman scattering unit has been problematic in that its surface-enhanced Raman scattering effect is likely to deteriorate before used, due to oxidation of the minute metal structure, adhesion of foreign matters and impurities to the minute metal structure, and the like.

It is therefore an object of the present invention to provide a surface-enhanced Raman scattering unit which can prevent its surface-enhanced Raman scattering effect from deteriorating before used and a method for using the same.

Solution to Problem

For achieving the above-mentioned object, the surface-enhanced Raman scattering unit in accordance with one aspect of the present invention comprises a substrate, an optical function part formed on the substrate, for generating surface-enhanced Raman scattering, and a package containing the optical function part in an inert space and configured to irreversibly expose the space.

In this surface-enhanced Raman scattering unit, the package contains the optical function part for generating surface-enhanced Raman scattering in the inert space. Therefore, unsealing the package immediately before used so as to open the space irreversibly can prevent the surface-enhanced Raman scattering effect from deteriorating.

In the surface-enhanced Raman scattering unit in accordance with one aspect of the present invention, the package may be configured to irreversibly expose the space in order to arrange a sample on the optical function part. This configuration can prevent the surface-enhanced Raman scattering effect from deteriorating before used by unsealing the package immediately before used as mentioned above and arranging the sample on the optical function part.

In the surface-enhanced Raman scattering unit in accordance with one aspect of the present invention, the package may be a cap attached onto the substrate. By utilizing the substrate, this configuration can simplify the structure of the package for containing the optical function part in the inert space and configured to irreversibly expose the space.

In the surface-enhanced Raman scattering unit in accordance with one aspect of the present invention, the cap may have a deformable part configured to deform according to a difference in pressure between the space and the outside of the cap. When the inert space is attained by raising the degree of vacuum, for example, this configuration makes it possible to determine according to the state of deformation of the deformable part whether or not the package is unsealed or whether or not a leak occurs before used.

In the surface-enhanced Raman scattering unit in accordance with one aspect of the present invention, the cap may be configured to irreversibly expose the space when a part of the cap is removed. This configuration makes it possible to utilize the part of the cap remaining on the substrate in order to arrange the sample stably on the optical function part and so forth.

In the surface-enhanced Raman scattering unit in accordance with one aspect of the present invention, the cap may have a tubular surrounding part attached onto the substrate while surrounding the optical function part, and an opposing part sealing an opening of the surrounding part while opposing the optical function part, the opposing part may be removed as the part of the cap from the surrounding part. This configuration makes it possible to utilize the surrounding part remaining on the substrate in order to arrange the sample stably on the optical function part and so forth.

In the surface-enhanced Raman scattering unit in accordance with one aspect of the present invention, the opposing part may have a thickness smaller than that of the surrounding part. This configuration makes it easy to remove the opposing part from the surrounding part when used, while securely keeping the inert space containing the optical function part before used.

In the surface-enhanced Raman scattering unit in accordance with one aspect of the present invention, a weakened part may be formed in a boundary part between the surrounding part and the opposing part. This configuration makes it easy to remove the opposing part from the surrounding part when used, while securely keeping the inert space containing the optical function part before used.

In the surface-enhanced Raman scattering unit in accordance with one aspect of the present invention, a plurality of such optical function parts may be formed on the substrate, the surrounding part and opposing part may be provided for the respective optical function parts. By removing only the opposing part corresponding to the optical function part to be used, this configuration can keep the other optical function parts in the inert spaces. It also becomes possible to measure a plurality of kinds of samples on the same substrate without mixing them. It can further save the trouble of replacing the surface-enhanced Raman scattering unit and so forth at the time of measurement, thereby improving operational efficiency.

The surface-enhanced Raman scattering unit in accordance with one aspect of the present invention may further comprise a holding member attached to the part of the cap. This configuration makes it possible to remove the part of the cap easily and securely by using the holding member.

In the surface-enhanced Raman scattering unit in accordance with one aspect of the present invention, the holding member may be attached to the part of the cap with a resin layer interposed therebetween. This configuration makes it possible to attach the holding member easily and securely to the part of the cap even when deflection and the like occur in the part of the cap.

In the surface-enhanced Raman scattering unit in accordance with one aspect of the present invention, the cap may be configured to irreversibly expose the space when a whole of the cap is removed from the substrate. This configuration can improve the strength of the whole cap in order to more securely keep the inert space containing the optical function part before used.

The surface-enhanced Raman scattering unit in accordance with one aspect of the present invention, a plurality of such optical function parts are formed on the substrate, a plurality of such caps may be attached onto the substrate for the respective optical function parts. By removing only the cap corresponding to the optical function part to be used, this configuration can keep the other optical function parts in the inert spaces. It also becomes possible to measure a plurality of kinds of samples on the same substrate without mixing them. It can further save the trouble of replacing the surface-enhanced Raman scattering unit and so forth at the time of measurement, thereby improving operational efficiency.

The surface-enhanced Raman scattering unit in accordance with one aspect of the present invention may further comprise a holding member attached to the cap. This configuration makes it possible to remove the cap easily and securely by using the holding member.

In the surface-enhanced Raman scattering unit in accordance with one aspect of the present invention, the holding member may be attached to the cap with a resin layer interposed therebetween. This configuration makes it possible to attach the holding member easily and securely to the cap even when deflection and the like occur in the cap.

The surface-enhanced Raman scattering unit in accordance with one aspect of the present invention may further comprise a handling board having the substrate attached thereto, the package may be a cap attached onto the handling board. By utilizing the handling board, this configuration can simplify the structure of the package for containing the optical function part in the inert space and configured to irreversibly expose the space.

In the surface-enhanced Raman scattering unit in accordance with one aspect of the present invention, the cap may have a deformable part configured to deform according to a difference in pressure between the space and the outside of the cap. When the inert space is attained by raising the degree of vacuum, for example, this configuration makes it possible to determine according to the state of deformation of the deformable part whether or not the package is unsealed or whether or not a leak occurs before used.

In the surface-enhanced Raman scattering unit in accordance with one aspect of the present invention, the cap may be configured to irreversibly expose the space when a part of the cap is removed. This configuration makes it possible to arrange the sample stably on the optical function part by utilizing the part of the cap remaining on the substrate.

In the surface-enhanced Raman scattering unit in accordance with one aspect of the present invention, the cap may have a tubular surrounding part attached onto the handling board while surrounding the substrate and optical function part, and an opposing part sealing an opening of the surrounding part while opposing the substrate and optical function part, the opposing part may be removed as the part of the cap from the surrounding part. This configuration makes it possible to utilize the surrounding part in order to arrange the sample stably on the optical function part and so forth.

In the surface-enhanced Raman scattering unit in accordance with one aspect of the present invention, the opposing part may have a thickness smaller than that of the surrounding part. This configuration makes it easy to remove the opposing part from the surrounding part when used, while securely keeping the inert space containing the optical function part before used.

In the surface-enhanced Raman scattering unit in accordance with one aspect of the present invention, a weakened part may be formed in a boundary part between the surrounding part and the opposing part. This configuration makes it easy to remove the opposing part from the surrounding part when used, while securely keeping the inert space containing the optical function part before used.

In the surface-enhanced Raman scattering unit in accordance with one aspect of the present invention, a plurality of such substrates may be attached onto the handling board, the surrounding part and opposing part may be provided for the respective substrates. By removing only the opposing part corresponding to the optical function part to be used, this configuration can keep the other optical function parts in the inert spaces. It also becomes possible to measure a plurality of kinds of samples on the same handling board without mixing them. It can further save the trouble of replacing the surface-enhanced. Raman scattering unit and so forth at the time of measurement, thereby improving operational efficiency.

The surface-enhanced Raman scattering unit in accordance with one aspect of the present invention may further comprise a holding member attached to the part of the cap. This configuration makes it possible to remove the part of the cap easily and securely by using the holding member.

In the surface-enhanced Raman scattering unit in accordance with one aspect of the present invention, the holding member may be attached to the part of the cap with a resin layer interposed therebetween. This configuration makes it possible to attach the holding member easily and securely to the part of the cap even when deflection and the like occur in the part of the cap.

In the surface-enhanced Raman scattering unit in accordance with one aspect of the present invention, the cap may be configured to irreversibly expose the space when a whole of the cap is removed from the handling board. This configuration can improve the strength of the whole cap in order to more securely keep the inert space containing the optical function part before used.

The surface-enhanced Raman scattering unit in accordance with one aspect of the present invention, a plurality of such substrates are attached onto the handling board, a plurality of such caps are attached onto the handling board for the respective substrates. By removing only the cap corresponding to the optical function part to be used, this configuration can keep the other optical function parts in the inert spaces. It also becomes possible to measure a plurality of kinds of samples on the same handling board without mixing them. It can further save the trouble of replacing the surface-enhanced Raman scattering unit and so forth at the time of measurement, thereby improving operational efficiency.

The surface-enhanced Raman scattering unit in accordance with one aspect of the present invention may further comprise a holding member attached to the cap. This configuration makes it possible to remove the cap easily and securely by using the holding member.

In the surface-enhanced Raman scattering unit in accordance with one aspect of the present invention, the holding member may be attached to the cap with a resin layer interposed therebetween. This configuration makes it possible to attach the holding member easily and securely to the cap even when deflection and the like occur in the cap.

In the surface-enhanced Raman scattering unit in accordance with one aspect of the present invention, the package may comprises a handling board having a depression containing the substrate and optical function part, the depression including an inner surface having the substrate attached thereto, and a sheet sealing an opening of the depression, the package may be configured to irreversibly expose the space when the sheet is removed from the handling board. By utilizing the handling board, this configuration can simplify the structure of the package for containing the optical function part in the inert space and configured to irreversibly expose the space. It can also arrange the sample on the optical function part stably by utilizing the depression.

In the surface-enhanced Raman scattering unit in accordance with one aspect of the present invention, the handling board may have a plurality of such depressions, each of the depressions containing the substrate and optical function part, and including an inner surface having the substrate attached thereto. By unsealing only the depression containing the optical function part to be used, this configuration can keep the optical function parts contained in the other depressions in the inert spaces. It also becomes possible to measure a plurality of kinds of samples on the same handling board without mixing them. It can further save the trouble of replacing the surface-enhanced Raman scattering unit and so forth at the time of measurement, thereby improving operational efficiency.

In the surface-enhanced Raman scattering unit in accordance with one aspect of the present invention, a plurality of such sheets may be provided for the respective depressions. By removing the sheet from the handling board for only the depression containing the optical function part to be used, this configuration can easily and securely unseal this depression and seal the other depressions.

In the surface-enhanced Raman scattering unit in accordance with one aspect of the present invention, the package may have a cap containing the substrate and optical function part, and a sheet sealing an opening of the cap, the package may be configured to irreversibly expose the space when the cap is deformed by an action of an external force so that the sheet is broken through the substrate. This configuration can improve the degree of freedom in handling the substrate and optical function part after they are taken out of the package.

In the surface-enhanced Raman scattering unit in accordance with one aspect of the present invention, an inner surface of the cap may be formed with a recess opposing the optical function part. This configuration can prevent the cap and the optical function part from interfering with each other when the substrate and optical function part are contained in or taken out of the package.

In the surface-enhanced Raman scattering unit in accordance with one aspect of the present invention, an inner surface of the cap may be formed with a projection opposing the substrate around the optical function part. This configuration can prevent the cap and the optical function part from interfering with each other when the substrate and optical function part are contained in or taken out of the package.

The surface-enhanced Raman scattering unit in accordance with one aspect of the present invention may further comprise a handling board having a cap serving as the package attached thereto, the substrate may be attached to an inner surface of the cap such that the optical function part opposes the handling board, the cap may be configured to irreversibly expose the space when a whole of the cap is removed from the handling board. This configuration can inhibit foreign matters and impurities from adhering to the optical function part when removing the cap as a whole from above the handling board.

In the surface-enhanced Raman scattering unit in accordance with one aspect of the present invention, a plurality of such caps may be attached onto the handling board, the substrate may be attached to the inner surface of the cap for the respective caps. By unsealing only the cap containing the optical function part to be used, this configuration can keep the optical function parts contained in the other caps in the inert spaces. It also becomes possible to measure a plurality of kinds of samples on the same handling board without mixing them. It can further save the trouble of replacing the surface-enhanced Raman scattering unit and so forth at the time of measurement, thereby improving operational efficiency.

The surface-enhanced Raman scattering unit in accordance with one aspect of the present invention may further comprise a holding member attached to the cap. This configuration makes it possible to remove the cap easily and securely by using the holding member.

In the surface-enhanced Raman scattering unit in accordance with one aspect of the present invention, the holding member may be attached to the cap with a resin layer interposed therebetween. This configuration makes it possible to attach the holding member easily and securely to the cap even when deflection and the like occur in the cap.

A method for using a surface-enhanced Raman scattering unit in accordance with one aspect of the present invention is a method for using a surface-enhanced Raman scattering unit comprising a substrate, an optical function part formed on the substrate, for generating surface-enhanced Raman scattering, and a package containing the optical function part in an inert space and configured to irreversibly expose the space, the method comprising a first step of irreversibly exposing the space by unsealing the package, a second step of arranging the sample on the optical function part after the first step, and a third step of irradiating the sample with excitation light after the second step.

In the method for using a surface-enhanced Raman scattering unit in accordance with one aspect of the present invention, the package contains the optical function part for generating surface-enhanced Raman scattering in the inert space before used. Therefore, unsealing the package immediately before used so as to open the space irreversibly can prevent the surface-enhanced Raman scattering effect from deteriorating before used.

Advantageous Effects of Invention

The present invention can provide a surface-enhanced Raman scattering unit which can prevent its surface-enhanced Raman scattering effect from deteriorating before used and a method for using the same.

BRIEF DESCRIPTION OF DRAWINGS

FIG. 32 is a sectional view of a modified example of the surface-enhanced Raman scattering unit in accordance with the second embodiment of the present invention;

FIG. 37 is a sectional view of a modified example of the surface-enhanced Raman scattering unit in accordance with the third embodiment of the present invention.

DESCRIPTION OF EMBODIMENTS

Figure 1:
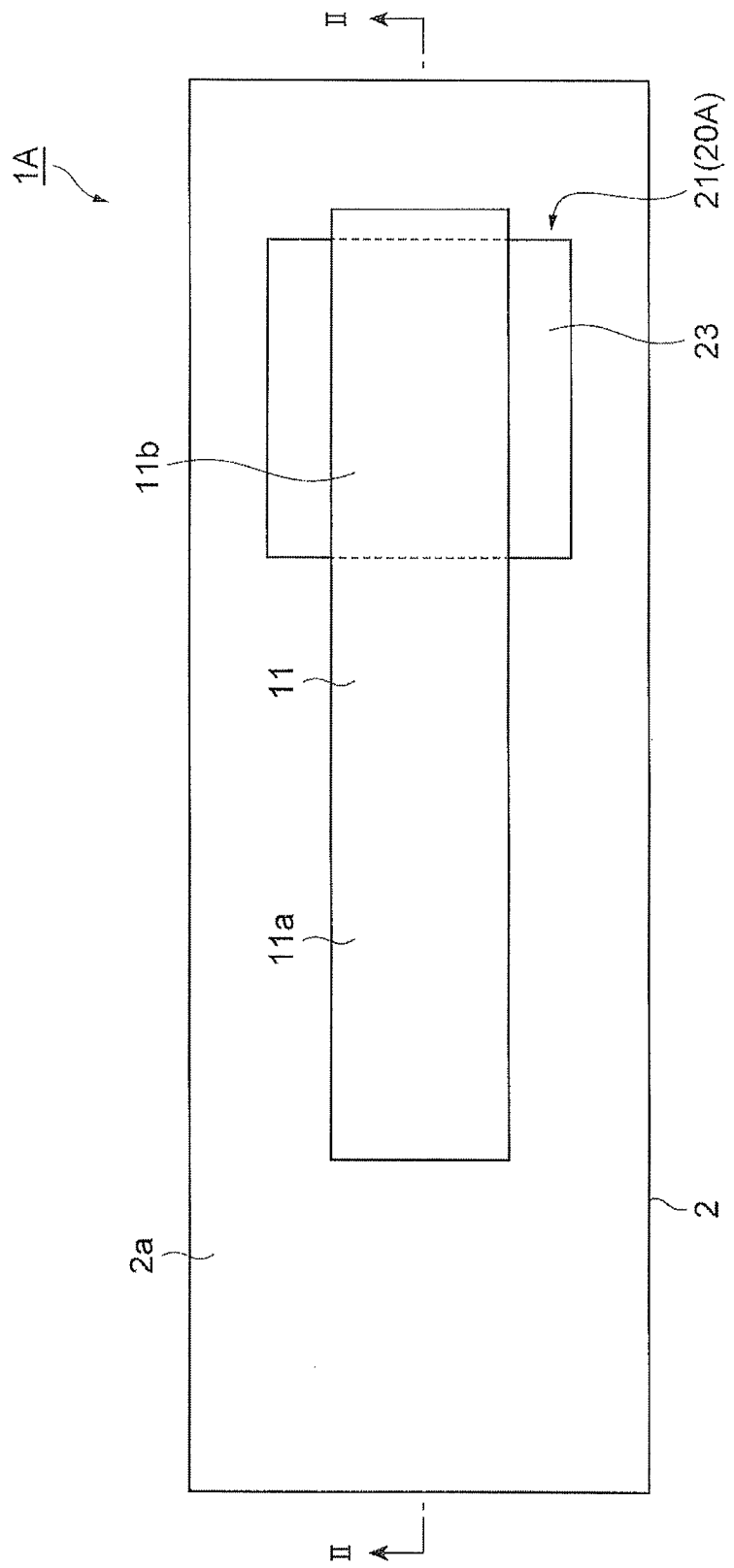
FIG. 1 is a plan view of the surface-enhanced Raman scattering unit in accordance with a first embodiment of the present invention.

In the following, preferred embodiments of the present invention will be explained in detail with reference to the drawings. In the drawings, the same or equivalent parts will be referred to with the same signs while omitting their overlapping descriptions.

First Embodiment

Figure 2:
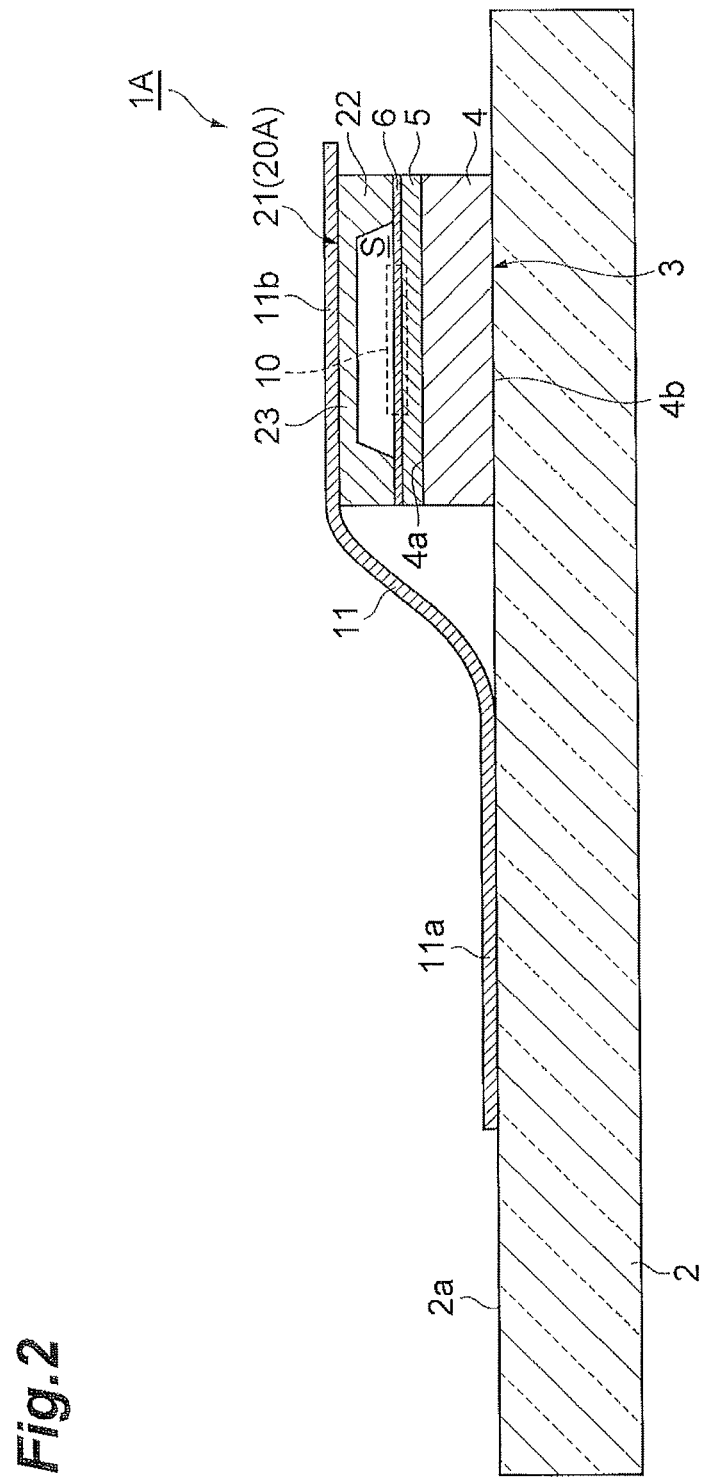
FIG. 2 is a sectional view taken along the line of FIG. 1.

As illustrated in FIGS. 1 and 2, a SERS unit (surface-enhanced Raman scattering unit) 1A comprises a handling board 2 and a SERS element (surface-enhanced Raman scattering element) 3 attached onto the handling board 2. The handling board 2 is a rectangular plate-shaped glass slide, resin board, ceramic board, or the like. The SERS element 3 is arranged on a front face 2a of the handling board 2 while being biased to one side in the longitudinal direction of the handling board 2.

The SERS element 3 comprises a substrate 4 attached onto the handling board 2, a molded layer 5 formed on the substrate 4, and a conductor layer 6 formed on the molded layer 5. The substrate 4 is formed into a rectangular plate by silicon, glass, or the like and has an outer form on the order of several hundred μm×several hundred μm to several ten mm×several ten mm and a thickness on the order of 100 μm to 2 mm. A rear face 4b of the substrate 4 is secured to the front face 2a of the handling board 2 by direct bonding, bonding with a metal such as solder, eutectic bonding, fusion bonding by irradiation with laser light and the like, anodic bonding, or bonding with a resin.

Figure 3:
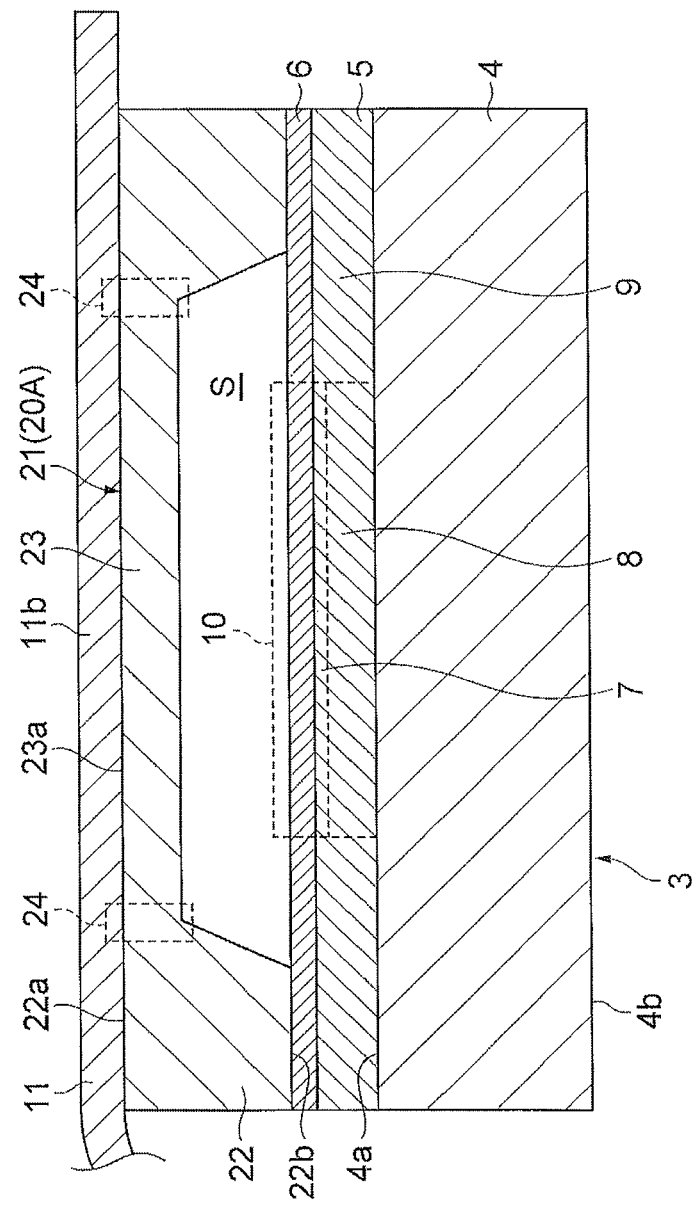
FIG. 3 is a partly enlarged sectional view of FIG. 2.

As illustrated in FIG. 3, the molded layer 5 includes a fine structure part 7, a support part 8, and a frame part 9. The fine structure part 7, which is a region having a periodic pattern, is formed on a surface layer on the side opposite from the substrate 4 at a center part of the molded layer 5. A plurality of pillars, each having a thickness and height on the order of several nm to several hundred nm, are periodically arranged at a pitch on the order of several ten nm to several hundred nm in the fine structure part 7. The fine structure part 7 has a rectangular outer form on the order of several hundred μm×several hundred μm to several ten mm×several ten mm when seen in the thickness direction of the substrate 4. The support part 8, which is a region for supporting the fine structure part 7, is formed on a front face 4a of the substrate 4. The frame part 9, which is a region surrounding the support part 8 like a ring, is formed on the front face 4a of the substrate 4. Each of the support part 8 and frame part 9 has a thickness on the order of several ten nm to several ten μm. The molded layer 5 like this is integrally formed by molding a resin (examples of which include resins based on acrylics, fluorine, epoxy, silicone, and urethane, PET, polycarbonate, and inorganic/organic hybrid materials) or lowmelting glass arranged on the substrate 4 by nanoimprinting, for example.

The conductor layer 6 is formed so as to extend over the fine structure part 7 and frame part 9. In the fine structure part 7, the conductor layer 6 reaches the surface of the support part 8 exposed to the side opposite from the substrate 4. The conductor layer 6 has a thickness on the order of several nm to several μm. The conductor layer 6 like this is formed by vapor-depositing a metal (Au, Ag, Al, Cu, Pt, or the like) on the molded layer 5 molded by nanoimprinting, for example. In the SERS element 3, the conductor layer 6 formed on the fine structure part 7 and the surface of the support part 8 exposed to the side opposite from the substrate 4 constructs an optical function part 10 which generates surface-enhanced Raman scattering.

Figure 36:
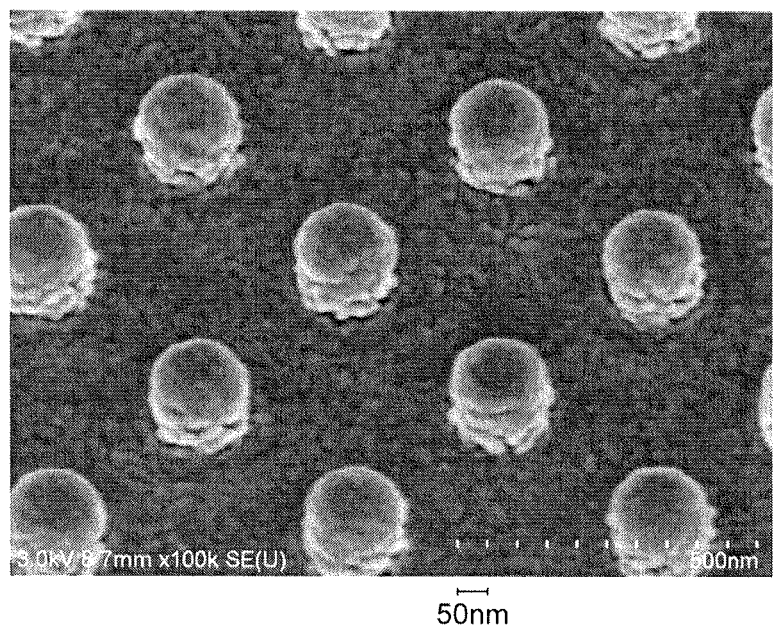
FIG. 36 is a SEM photograph of an optical function part in the surface-enhanced Raman scattering unit of FIG. 1.

A SEM photograph of the optical function part 10 is shown for reference. The optical function part shown in FIG. 36 is one in which Au was vapor-deposited as a conductor layer so as to yield a thickness of 50 nm in a fine structure part made of a nanoimprinting resin having a plurality of pillars (each having a diameter of 120 nm and a height of 180 nm) periodically arranged at a predetermined pitch (center line distance of 360 nm).

As illustrated in FIGS. 1 and 2, the SERS unit 1A further comprises a package 20A which contains the optical function part 10 formed on the substrate 4 in an inert space S. The package 20A is configured to irreversibly expose the space S in order to arrange a sample to be subjected to Raman spectroscopy on the optical function part 10. The space S is made an inert space by raising its degree of vacuum, being filled with an inert gas, or constructing the package 20A (mounting a cap 21, which will be explained later, here) in an atmosphere with less foreign matters and impurities. By "the package is configured to irreversibly expose the space" is meant herein that the package cannot return to its original state after being unsealed (i.e., cannot be reconstructed) and that the space opened by unsealing the package cannot return to the original inert space.

As illustrated in FIG. 3, the package 20A is the cap 21 attached onto the SERS element 3. The cap 21 is attached onto the substrate 4 with the frame part 9 of the molded layer 5 and the conductor layer 6 interposed therebetween. The cap 21 has a surrounding part 22 formed like a rectangular tube attached onto the substrate 4 while surrounding the optical function part 10 and a film-shaped opposing part 23 sealing the opening of the surrounding part 22 while opposing the optical function part 10. An end face 22b on the substrate 4 side of the surrounding part 22 is secured to the front face of the conductor layer 6 by direct bonding, bonding with a metal such as solder, eutectic bonding, fusion bonding by irradiation with laser light and the like, anodic bonding, or bonding with a resin. The surrounding part 22 and opposing part 23 are integrally formed by silicon, glass, or the like and define the space S shaped into a truncated quadrangular pyramid widening toward the substrate 4.

As illustrated in FIGS. 1 and 2, the SERS unit 1A further comprises a seal member (holding member) 11 attached to a part of the cap 21. A base end part 11a of the seal member 11 is bonded to the front face 2a of the handling board 2. A leading end part 11b of the seal member 11 is bonded to a surface 23a of the opposing part 23 on the opposite side of the substrate 4 in the cap 21 (see FIG. 3), while a part of the leading end part 11b protrudes from the upper side of the cap 21. The base end part 11a of the seal member 11 is not required to be bonded to the front face 2a of the handling board 2.

Figure 4:
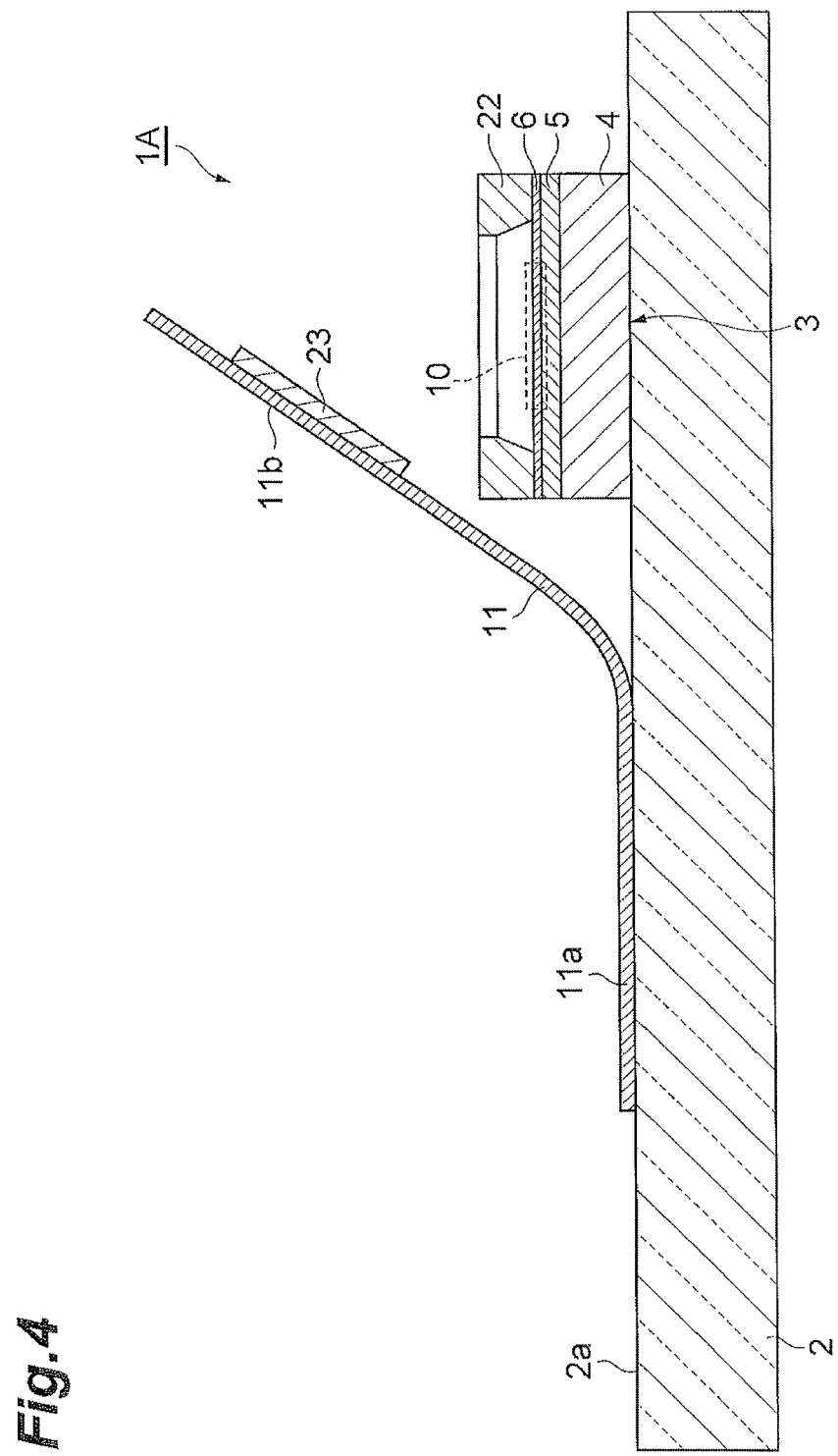
FIG. 4 is a sectional view illustrating a step of using the surface-enhanced Raman scattering unit of FIG. 1.

As illustrated in FIG. 3, the opposing part 23 is made thinner than the surrounding part 22 in the cap 21. By way of example, the thickness of the opposing part 23 is on the order of several μm to 100 μm, while the thickness of the surrounding part 22 is on the order of 0.3 mm to 2 mm. A weakened part 24 is further formed in a boundary part between the surrounding part 22 and opposing part 23. When a part of the leading end part 11b of the seal member 11 is held and lifted, the opposing part 23 having the leading end part 11b of the seal member 11 attached thereto also rises as illustrated in FIG. 4. At this time, the cap 21 breaks at the boundary part between the surrounding part 22 and opposing part 23 from the weakened part 24 serving as a start point, whereby the opposing part 23 having the leading end part 11b of the seal member 11 attached thereto is removed from the surrounding part 22. Thus, the package 20A irreversibly exposes the space S by removing the opposing part 23 from the surrounding part 22. The base end part 11a of the seal member 11 may be held and lifted instead of the leading end part 11b of the seal member 11.

The weakened part 24 is a region where the strength is reduced or stresses are likely to concentrate and becomes a start point for breaking the cap 21. Examples or the weakened part 24 include modified regions formed within the boundary part between the surrounding part 22 and opposing part 23 along the boundary part and cuts, cracks, and grooves formed on the surface of the boundary part between the surrounding part 22 and opposing part 23 along the boundary part. The modified regions are formed by irradiation with laser light. The cuts, cracks, and grooves are formed by machining or etching.

A method for using the SERS unit 1A will now be explained. First, as illustrated in FIG. 4, a part of the leading end part 11b of the seal member 11 is held and lifted, so as to remove the opposing part 23 from the surrounding part 22. Thus, the package 20A is unsealed, so as to open the space S irreversibly (first step).

Figure 5:
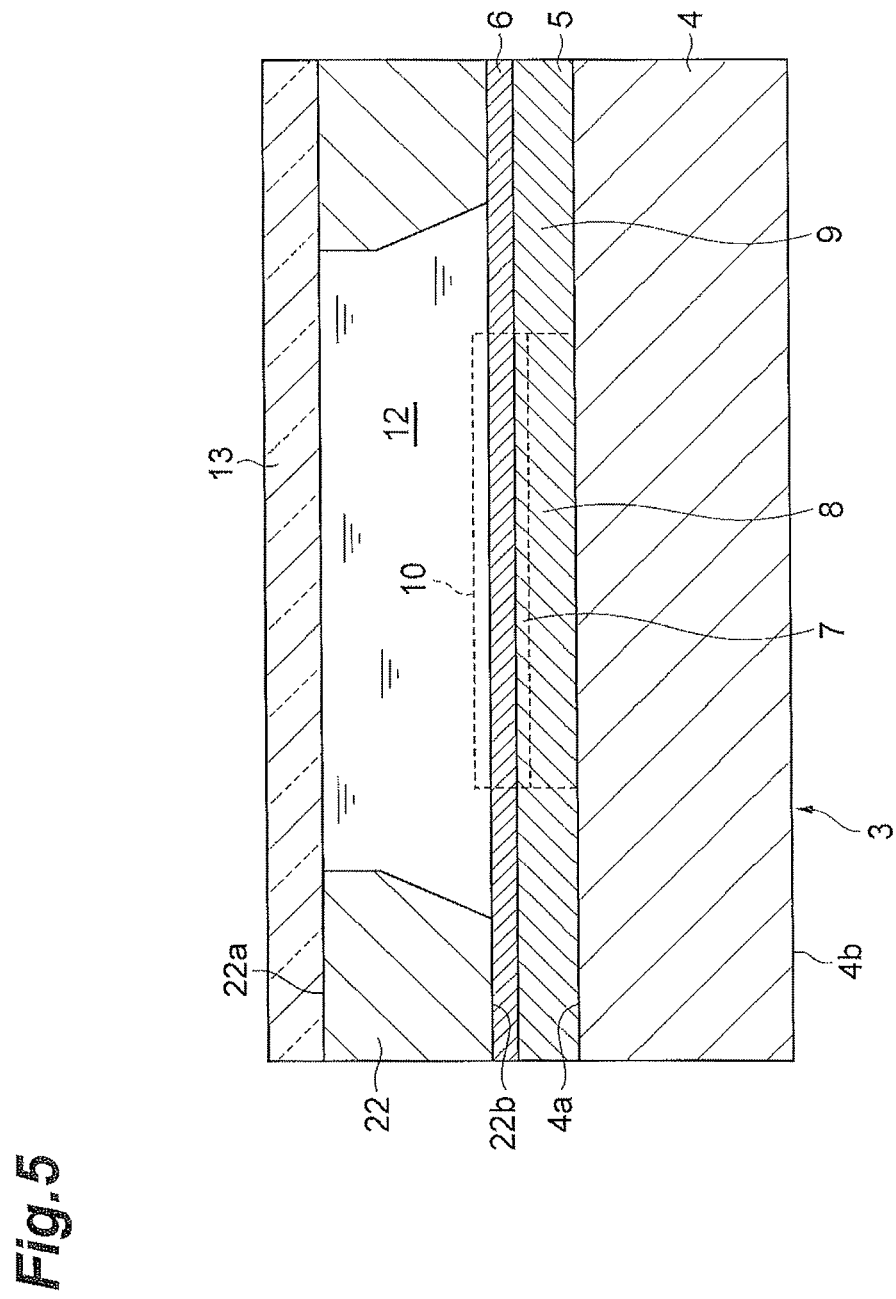
FIG. 5 is a partly enlarged sectional view illustrating a step of using the surface-enhanced Raman scattering unit of FIG. 1.

Subsequently, as illustrated in FIG. 5, a sample 12 of a solution (or a dispersion of a powder sample in a solution such as water or ethanol) is dropped to the inside of the surrounding part 22 with a pipette or the like, so as to be arranged on the optical function part 10 (second step). Thus, the surrounding part 22, which is a part of the cap 21, can be utilized as a cell (chamber) for the solution sample 22. Then, for reducing the lens effect, a glass cover 13 is mounted on the end face 22a of the surrounding part 22 on the opposite side of the substrate 4 and brought into close contact with the solution sample 12. Thus, the surrounding part 22, which is a part of the cap 21, can be utilized as a mount table for the glass cover 13.

Next, the SERS unit 1A is set in a Raman spectroscopic analyzer, and the sample 12 arranged on the optical function part 10 is irradiated with excitation light through the glass cover 13 (third step). This generates surface-enhanced Raman scattering at the interface between the optical function part 10 and sample 12, whereby surface-enhanced Raman scattering light derived from the sample 12 is enhanced by about $10^8$ times, for example, and released. Hence, the Raman spectroscopic analyzer enables Raman spectroscopy with high sensitivity and high accuracy.

Not only the above-mentioned method, but the following methods may also be used for arranging the sample on the optical function part 10. For example, while holding the handling board 2, the SERS element 3 may be dipped in and lifted from the solution sample (or a dispersion of a powder sample in a solution such as water or ethanol), and then the sample may be blown to dry. A minute amount of the solution sample (or a dispersion of a powder sample in a solution such as water or ethanol) may be dropped onto the optical function part 10 and left to dry. A powder sample may be dispersed as it is on the optical function part 10. In these cases, it is not necessary for the glass cover 13 to be arranged at the time of measurement.

Figure 6:
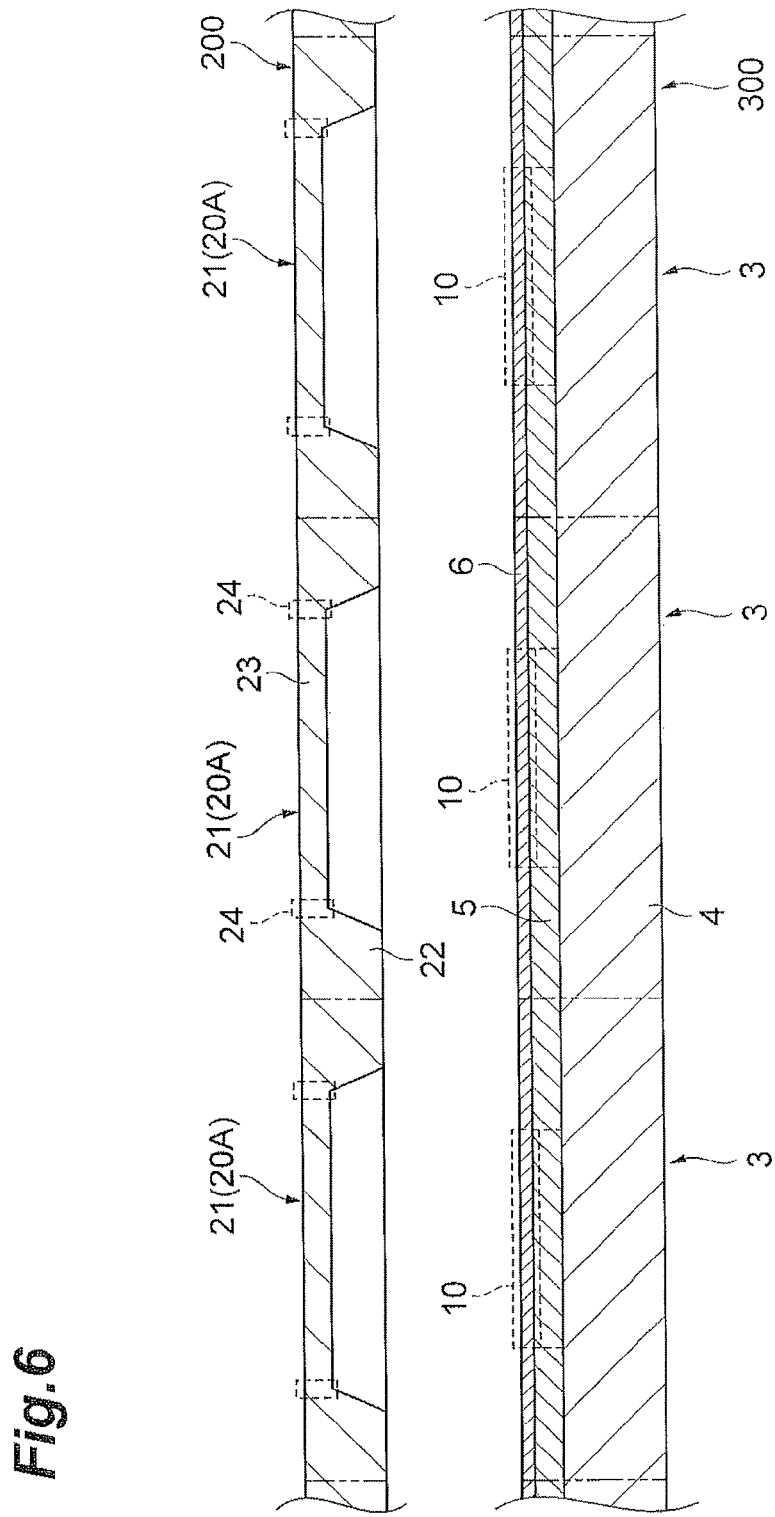
FIG. 6 is a sectional view illustrating a step of using the surface-enhanced Raman scattering unit of FIG. 1.

A method for manufacturing the SERS unit 1A will now be explained. First, as illustrated in FIG. 6, a wafer 300 including a plurality of parts to become SERS elements 3 is prepared. The parts to become the SERS elements 3 in the wafer 300 are arranged into a matrix. The wafer 300 like this is produced by performing molding by nanoimprinting and vapor deposition of a metal and the like on a wafer level. On the other hand, a wafer 200 including a plurality of parts to become caps 21 is prepared. The parts to become the caps 21 in the wafer 200 are arranged into a matrix as with the parts to become the SERS elements 3 in the wafer 300. The wafer 200 like this is produced by performing etching, blasting, or the like on a wafer level.

Figure 7:
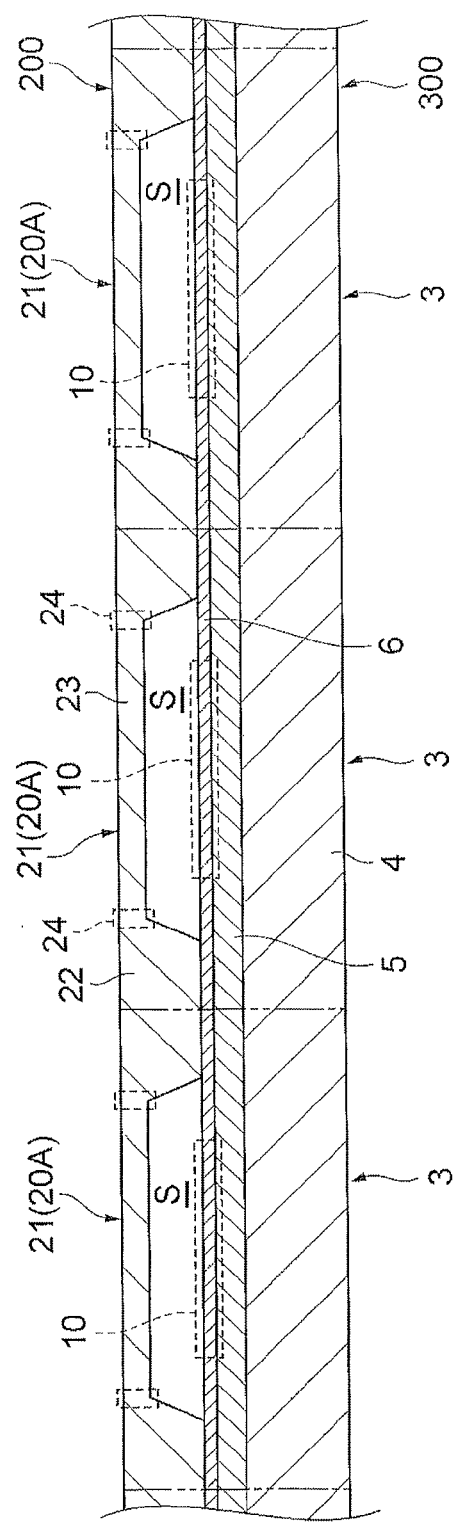
FIG. 7 is a sectional view illustrating a step of using the surface-enhanced Raman scattering unit of FIG. 1.

Subsequently, as illustrated in FIG. 7, the wafers 200, 300 are secured to each other by direct bonding, bonding with a metal such as solder, eutectic bonding, fusion bonding by irradiation with laser light and the like, anodic bonding, or bonding with a resin in a vacuum, an inert gas atmosphere, or an atmosphere with less foreign matters and impurities such that the parts to become the SERS elements 3 and the parts to become the caps 21 correspond to each other. As a consequence, the optical function parts 10 are contained in the respective inert spaces S.

Figure 8:
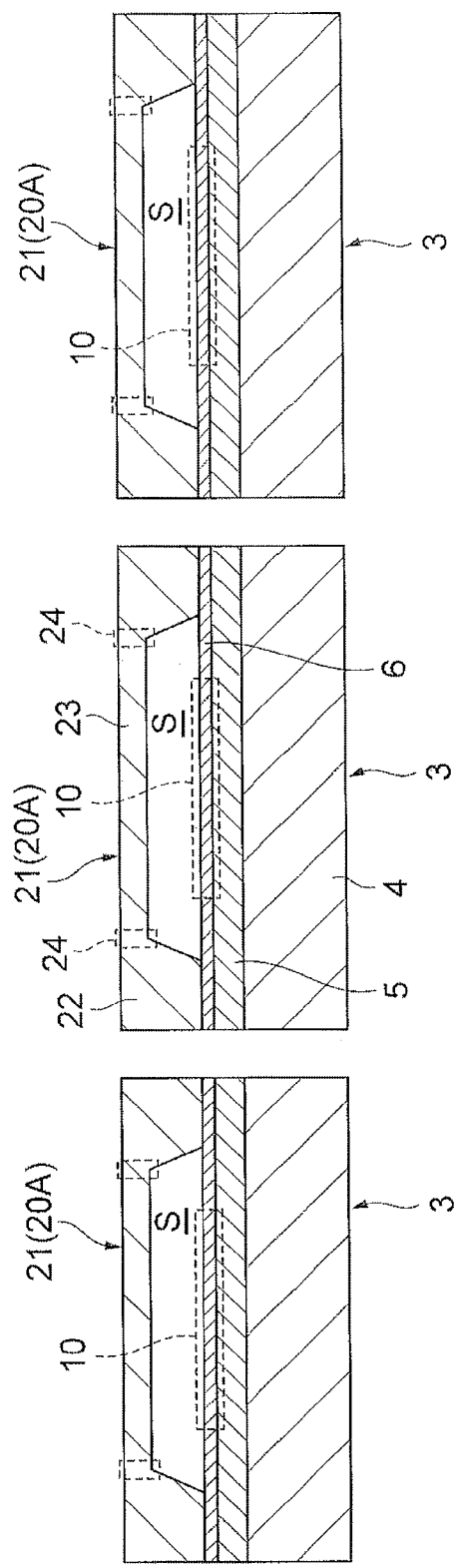
FIG. 8 is a sectional view illustrating a step of using the surface-enhanced Raman scattering unit of FIG. 1.

Next, as illustrated in FIG. 8, the wafers 200, 300 are diced for each part to become the SERS element 3 (i.e., each part to become the cap 21). This produces a plurality of SERS elements 3 having the respective caps 21 attached thereto. Each optical function part 10 is thus contained in the inert space S at the time of dicing the wafers 200, 300 and therefore can be prevented from deteriorating due to foreign matters and impurities attached thereto and the like. Subsequently, the SERS element 3 is secured to the handling board 2 by direct bonding, bonding with a metal such as solder, eutectic bonding, fusion bonding by irradiation with laser light and the like, anodic bonding, or bonding with a resin. Then, the base end part 11a of the seal member 11 is bonded to the front face 2a of the handling board 2, and the leading end part 11b of the seal member 11 is bonded to the surface 23a of the opposing part 23 of the cap 21. The foregoing manufactures the SERS unit 1A.

Effects exhibited by the SERS unit 1A will now be explained. First, in the SERS unit 1A, the package 20A contains the optical function part 10 for generating surface-enhanced Raman scattering in the inert space S. Therefore, irreversibly exposing the space S by unsealing the package 20A immediately before used can prevent the surface-enhanced Raman scattering effect from deteriorating (e.g., the surface-enhanced Raman scattering effect from deteriorating due to foreign matters and impurities attached to the optical function part 10) before used.

Here, in the SERS unit 1A, a sample (e.g., molecular sample) to be subjected to Raman spectroscopy comes into close contact with the surface of the conductor layer 6 in the optical function part 10, whereby effective surface-enhanced Raman scattering can occur, which makes it very important to prevent the surface of the conductor layer 6 from being contaminated. Examples of the contamination include adhesion of organic matters from within the air, adhesion of moisture, oxidation of the surface of the conductor layer 6 caused by adsorption of moisture, and adhesion of minute particles; when the surface of the conductor layer 6 is contaminated by them, the sample is inhibited from coming into contact with the surface of the conductor layer 6, whereby effective surface-enhanced Raman scattering cannot occur. Therefore, the inert space S is a space produced by raising its degree of vacuum, being filled with an inert gas, or constructing the package 20A in an atmosphere with less foreign matters and impurities, for example, so as to be blocked from communicating with the external atmosphere immediately before opening, whereby the above-mentioned contamination is harder to occur (i.e., the surface of the conductor layer 6 in the optical function part 10 is less likely to be contaminated than in the external atmosphere).

Since the package 20A is the cap 21 attached onto the substrate 4 of the SERS element 3, the substrate 4 can be utilized so as to simplify the structure of the package 20A containing the optical function part 10 in the inert space S and configured to irreversibly expose the space S.

Since the cap 21 is configured to irreversibly expose the space S by removing the opposing part 23 from the surrounding part 22, the surrounding part 22 remaining on the substrate 4 can be utilized for stably arranging the sample on the optical function part 10 and the like.

Since the opposing part 23 is made thinner than the surrounding part 22, and the weakened part 24 is formed in the boundary part between the surrounding part 22 and opposing part 23, the opposing part 23 can easily be removed from the surrounding part 22 when used, while the inert space S containing the optical function part 10 can securely be kept before used. Thinning the opposing part 23 or forming the weakening part 24 may be performed alone as long as the opposing part 23 can easily be removed from the surrounding part 22 when used.

Since the seal member 11 is attached to the opposing part 23 that is removed when used, the opposing part 23 can be removed easily and securely from the cap 21 by using the seal member 11 when used, so as to avoid the optical function part 10 from being contaminated due to dropout of the opposing part 23 onto the optical function part 10 and the like.

Figure 9:
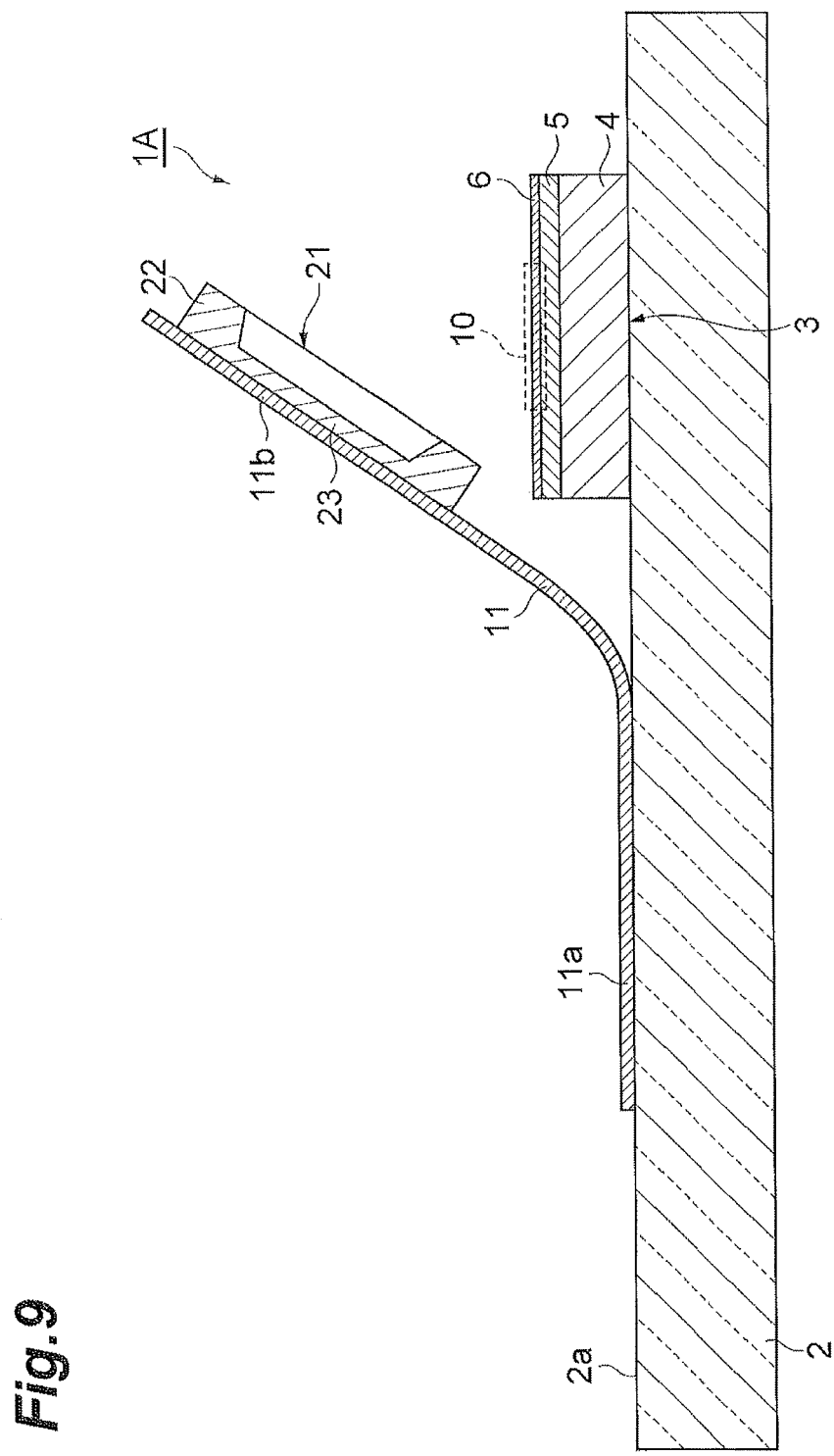
FIG. 9 is a sectional view illustrating a step of using a modified example of the surface-enhanced Raman scattering unit in accordance with the first embodiment of the present invention.

Modified examples of the above-mentioned SERS unit 1A will now be explained. As illustrated in FIG. 9, the cap 21 may be configured to irreversibly expose the space S by being removed as a whole from above the substrate 4. That is, when a part of the leading end part 11b of the seal member 11 is held and lifted when used, the joint between the end face 22b of the surrounding part 22 and the surface of the conductor layer 6 of the SERS element 3 breaks, whereby the cap 21 as a whole is removed from above the substrate 4. In this case, the weakened part 24 is not formed in the boundary part between the surrounding part 22 and opposing part 23. It is also unnecessary for the opposing part 23 to be made thinner. For arranging the solution sample 12 (or a dispersion of a powder sample in a solution such as water or ethanol) on the optical function part 10, a spacer formed into a shape equivalent to that of the surrounding part 22 from silicone, for example, may be arranged on the substrate 4.

This configuration makes it unnecessary to form the weakened part 24 or thin the opposing part 23 more than necessary in order for the opposing part 23 to be removed easily from the surrounding part 22 when used. Hence, the strength of the cap 21 as a whole can be improved so that the inert space S containing the optical function part 10 can be kept more securely before used.

Figure 10:
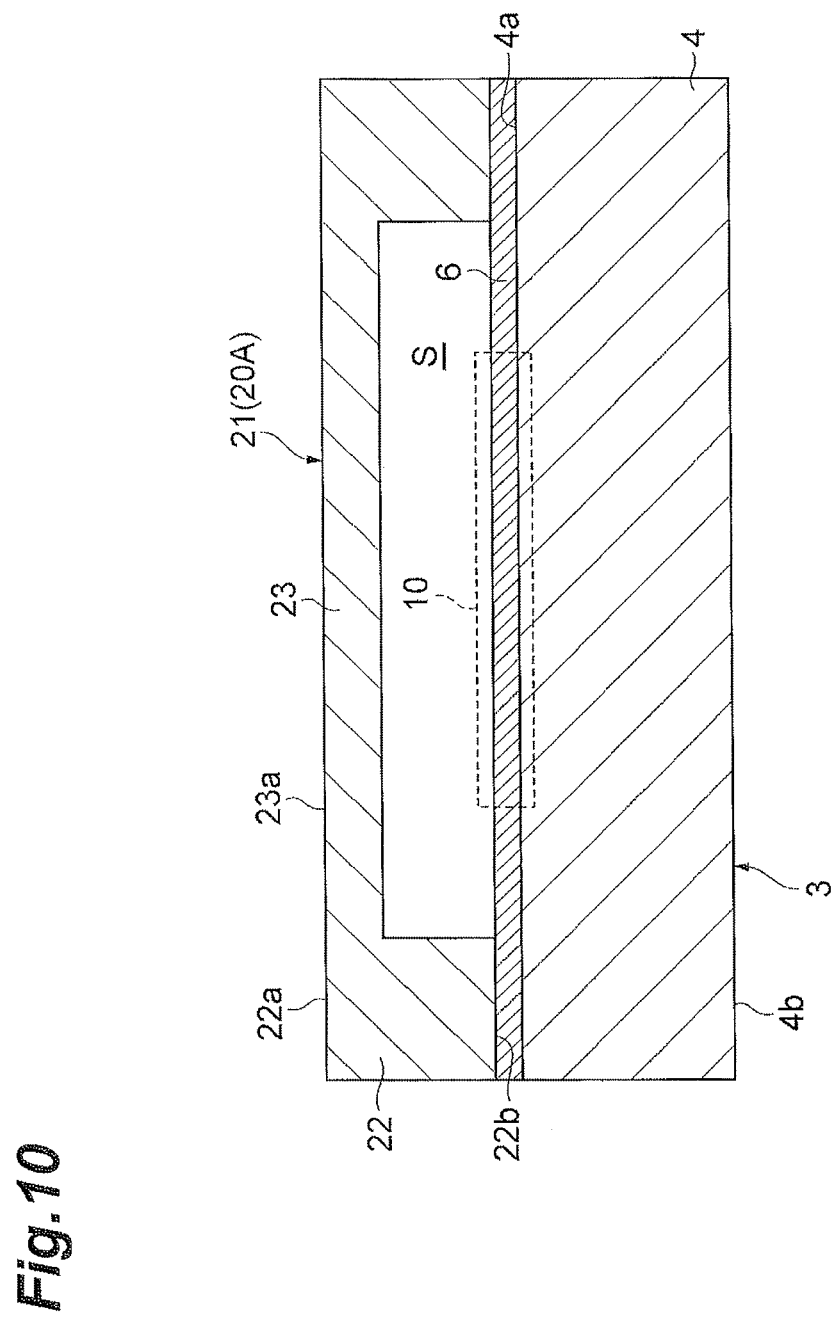
FIG. 10 is a partly enlarged sectional view of a modified example of the surface-enhanced Raman scattering unit in accordance with the first embodiment of the present invention.
Figure 11:
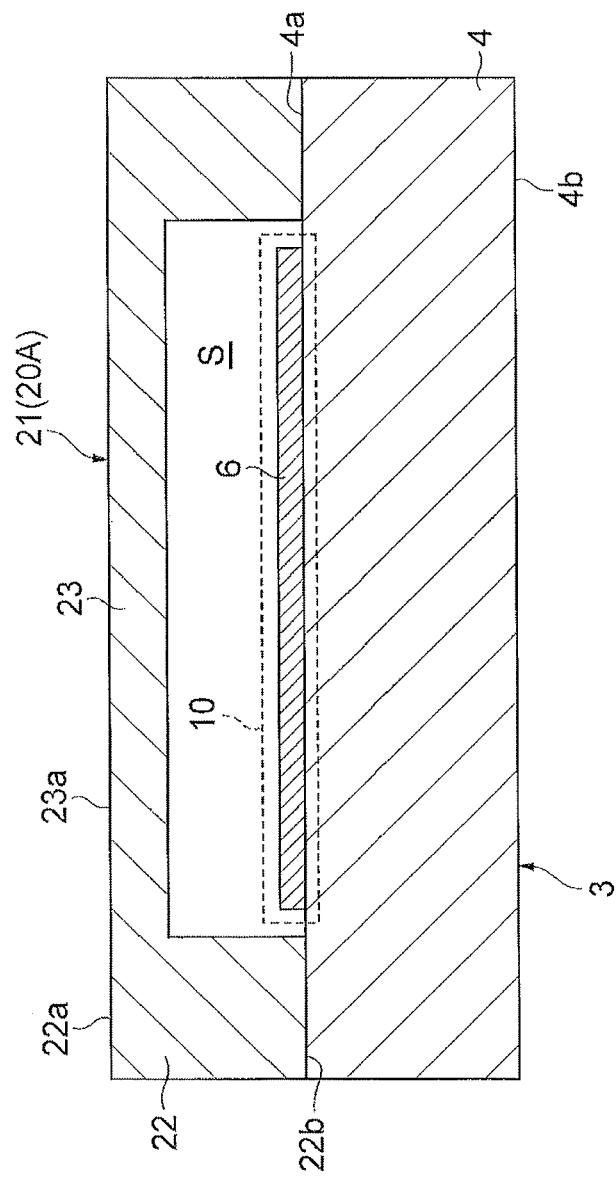
FIG. 11 is a partly enlarged sectional view of a modified example of the surface-enhanced Raman scattering unit in accordance with the first embodiment of the present invention.

As illustrated in FIG. 10, the conductor layer 6 may directly be formed on the front face 4a of the substrate 4. In this case, a fine structure part is formed on the front face 4a of the substrate 4 by nanoimprinting, etching, anodic oxidation, laser ablation, or the like, and then the conductor layer 6 is formed on the front face 4a of the substrate 4 by vapor deposition of a metal or the like. As illustrated in FIG. 11, the end face 22b of the surrounding part 22 may be secured to the front face 4a of the substrate 4 exposed in a part other than the optical function part 10. This configuration can prevent external forces from acting on the conductor layer 6 and causing the conductor 6 to peel off at the time of unsealing the package 20A. The surrounding part 22 and opposing part 23 may define the space S formed into a quadrangular prism instead of a truncated quadrangular pyramid. This configuration makes it easier for fractures to occur in the boundary part between the surrounding part 22 and opposing part 23 and thus is effective when removing the opposing part 23 from the surrounding part 22.

When the case of securing the cap 21 to the conductor layer 6 and the case of securing the cap 21 to the substrate 4 are compared with each other, the latter is more likely to yield a higher securing force than the former by utilizing direct bonding, for example. Therefore, it can be said preferable to secure the cap 21 to the substrate 4 when unsealing the package 20A by removing a part of the cap 21. When unsealing the package 20A by removing the cap 21 as a whole, on the other hand, it can be said preferable to secure the cap 21 to the conductor layer 6.

Whether being secured to the conductor layer 6 or the substrate 4, the cap 21 is harder to keep airtightness when joined with a resin than by direct bonding, bonding with a metal such as solder, eutectic bonding, or anodic bonding. Therefore, when securing the cap 21 by joining with a resin, it can be said preferable to achieve the inert space S by filling with an inert gas so as to yield a pressure on a par with the atmospheric pressure or constructing the package 20A in an atmosphere with less foreign matters and impurities than by raising the degree of vacuum.

Figure 12:
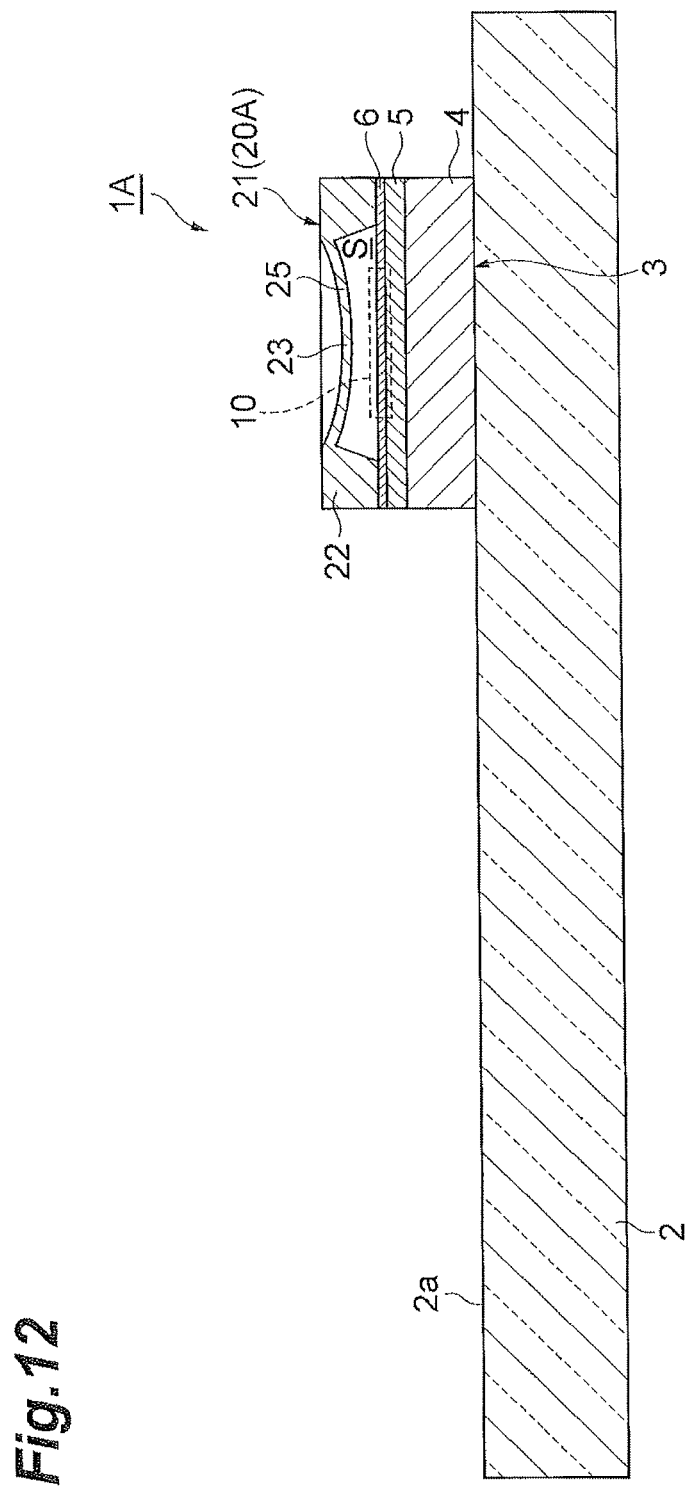
FIG. 12 is a sectional view of a modified example of the surface-enhanced Raman scattering unit in accordance with the first embodiment of the present invention.

As illustrated in FIG. 12, the cap 21 attached onto the substrate 4 may have a deformable part 25 configured to deform according to a difference in pressure between the space S and the outside of the cap 21. Here, the opposing part 23 having a thickness smaller than that of the surrounding part 22 also serves as the deformable part 25 and achieves the inert space S by raising the degree of vacuum. Hence, the deformable part 25 is deformed so as to be depressed. When the inert space S is achieved by filling with an inert gas so as to yield a pressure exceeding the atmospheric pressure, the deformable part 25 deforms so as to inflate. This configuration makes it possible to determine according to the state of deformation of the deformable part 25 whether or not the package 20A is unsealed or whether or not a leak occurs before used.

Figure 13:
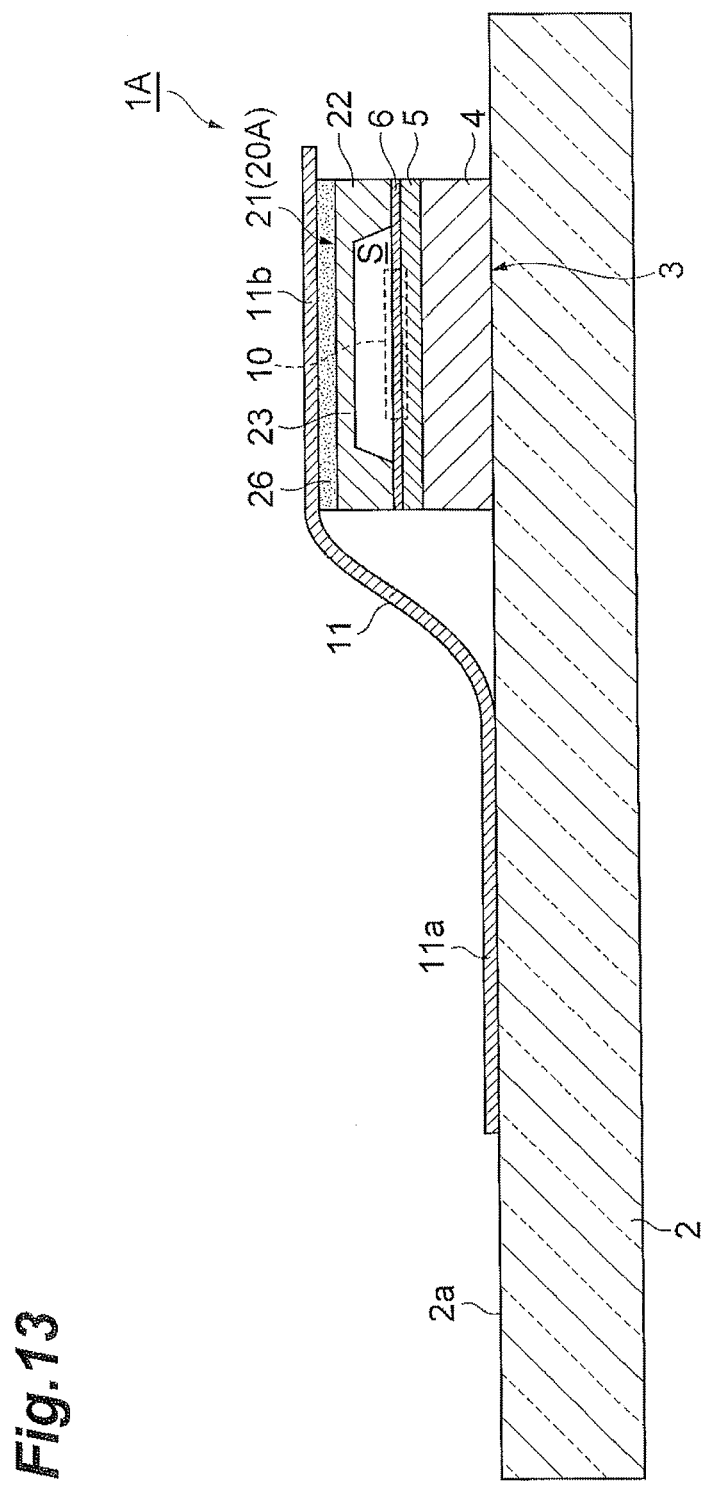
FIG. 13 is a sectional view of a modified example of the surface-enhanced Raman scattering unit in accordance with the first embodiment of the present invention.

As illustrated in FIG. 13, the seal member 11 may be attached to a part of the cap 21 with a resin layer 26 interposed therebetween. Here, the leading end part 11b of the seal member 11 is attached to the opposing part 23 with the resin layer 26 interposed therebetween. This configuration makes it possible to attach the leading end part 11b of the seal member 11 easily and securely to the opposing part 23 even when deflection and the like occur in the opposing part 23.

Figure 14:
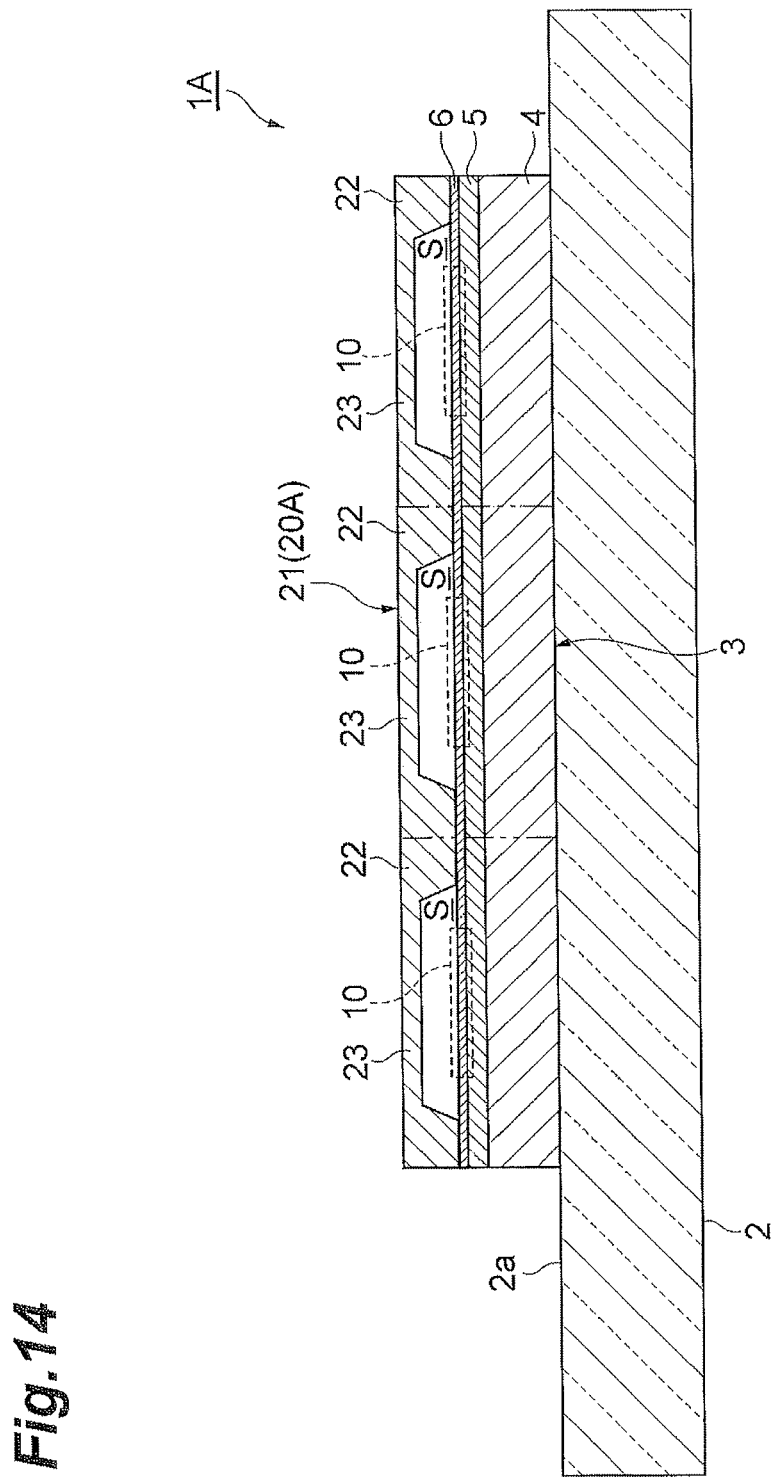
FIG. 14 is a sectional view of a modified example of the surface-enhanced Raman scattering unit in accordance with the first embodiment of the present invention.
Figure 15:
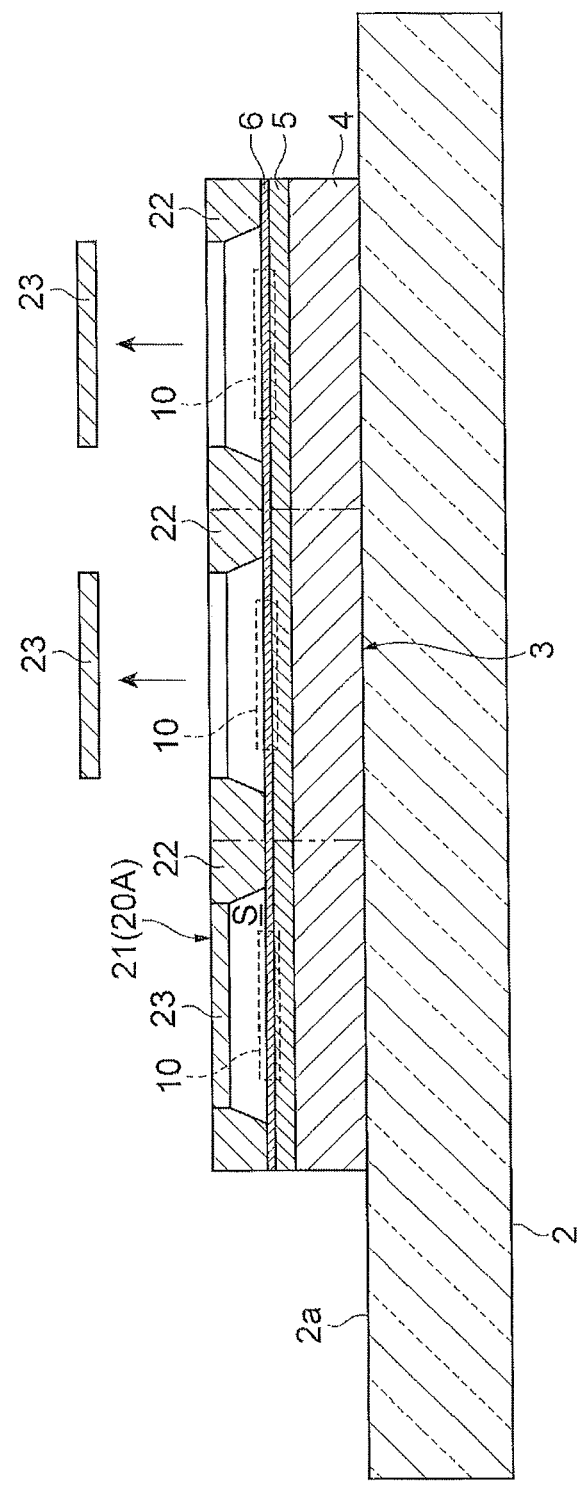
FIG. 15 is a sectional view illustrating a step of using the surface-enhanced Raman scattering unit of FIG. 14.

When a plurality of optical function parts 10 are formed on the substrate 4 in the case where the package 20A is unsealed by removing the opposing part 23 from the surrounding part 22, the surrounding part 22 and opposing part 23 may be provided for each optical function part 10 as illustrated in FIG. 14. In this case, the surrounding parts 22 adjacent to each other may be formed either continuously and integrally or separately from each other with a gap therebetween. By attaching the seal member 11 to each opposing part 23 and removing only the opposing parts 23 corresponding to the optical function parts 10 to be used from the surrounding parts 22, this configuration can keep the other optical function part 10 in the inert space S as illustrated in FIG. 15. It can also arrange different samples in the respective optical function parts 10 by removing a plurality of opposing parts 23 from the surrounding parts 22. Thus, a plurality of kinds of samples can be measured on the same substrate 4 without being mixed. It can further save the trouble of replacing the SERS unit 1A and so forth at the time of measurement, thereby improving operational efficiency.

When a plurality of optical function parts 10 are formed on the substrate 4 in the case where the package 20A is unsealed by removing the cap 21 as a whole from above the substrate 4, a plurality of caps 21 may be attached onto the substrate 4 for the respective optical function parts 10. In this case, it is necessary for the surrounding parts 22 adjacent to each other to be formed separately from each other with a gap therebetween. By attaching the seal members 11 to the respective caps 21 and removing only the cap 21 corresponding to the optical function part 10 to be used from above the substrate 4, this configuration can keep the other optical function parts 10 in the inert spaces S. It can also arrange different samples in the respective optical function parts 10 by removing a plurality of caps 21 from above the substrate 4. Thus, a plurality of kinds of samples can be measured on the same substrate 4 without being mixed. It can further save the trouble of replacing the SERS unit 1A and so forth at the time of measurement, thereby improving operational efficiency.

Second Embodiment

Figure 16:
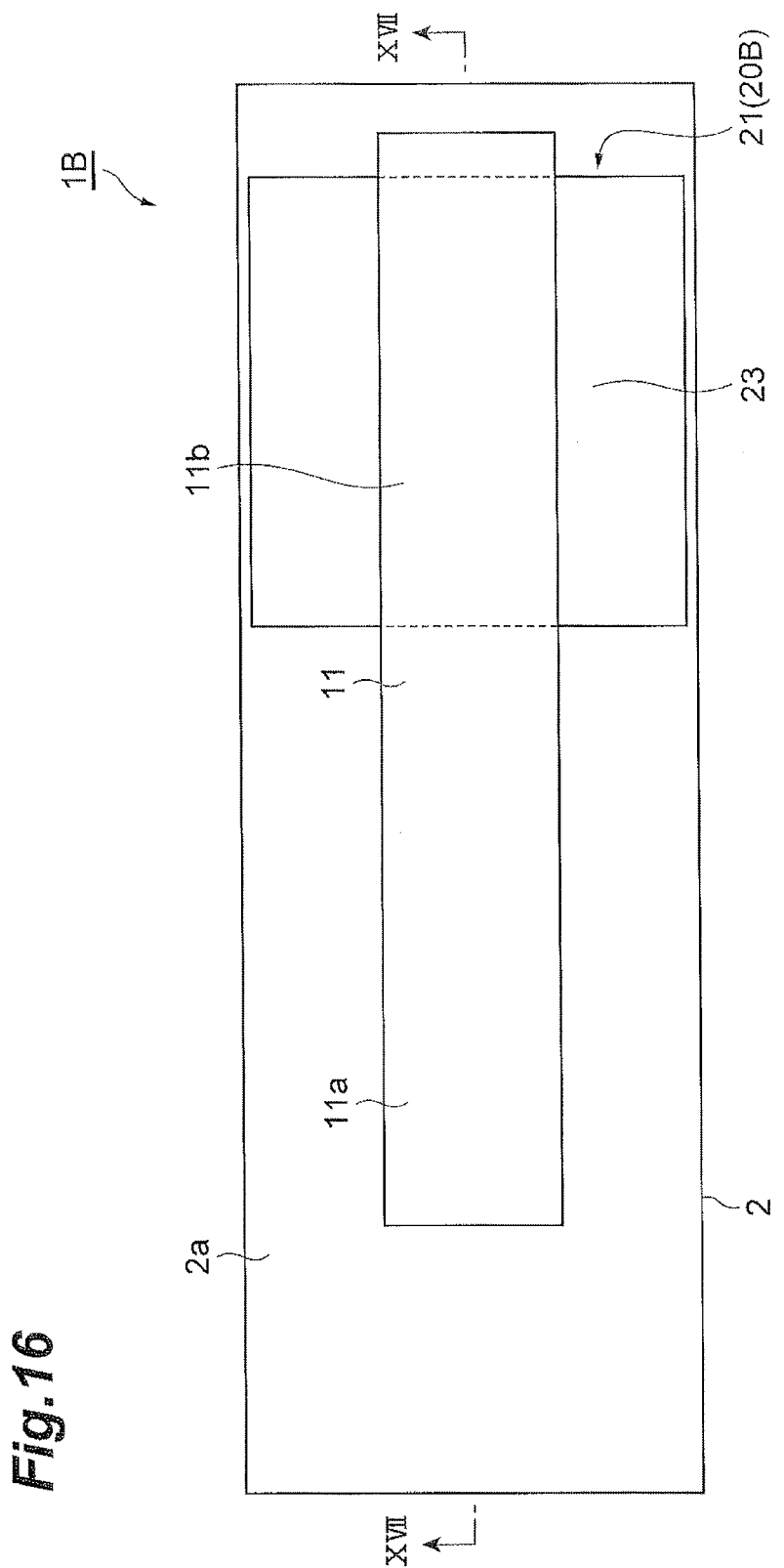
FIG. 16 is a plan view of the surface-enhanced Raman scattering unit in accordance with a second embodiment of the present invention.
Figure 17:
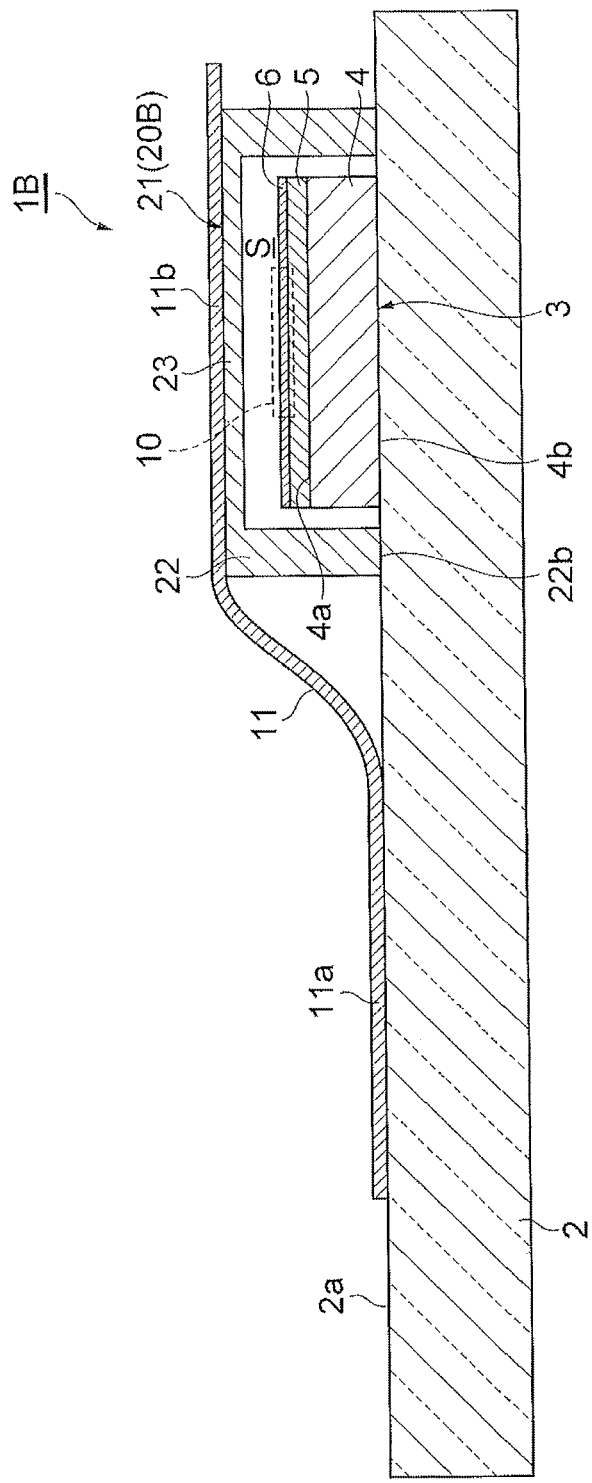
FIG. 17 is a sectional view taken along the line XVII-XVII of FIG. 16.

As illustrated in FIGS. 16 and 17, a SERS unit 1B differs from the above-mentioned SERS unit 1A mainly in that the cap 21 is attached onto the handling board 2. In the SERS unit 1B, a package 20B for containing the optical function part 10 formed on the substrate 4 in the inert space S is the cap 21 attached onto the handling board 2. The end face 22b of the surrounding part 22 of the cap 21 is secured to the front face 2a of the handling board 2 by direct bonding, bonding with a metal such as solder, eutectic bonding, fusion bonding by irradiation with laser light and the like, anodic bonding, or bonding with a resin.

Figure 18:
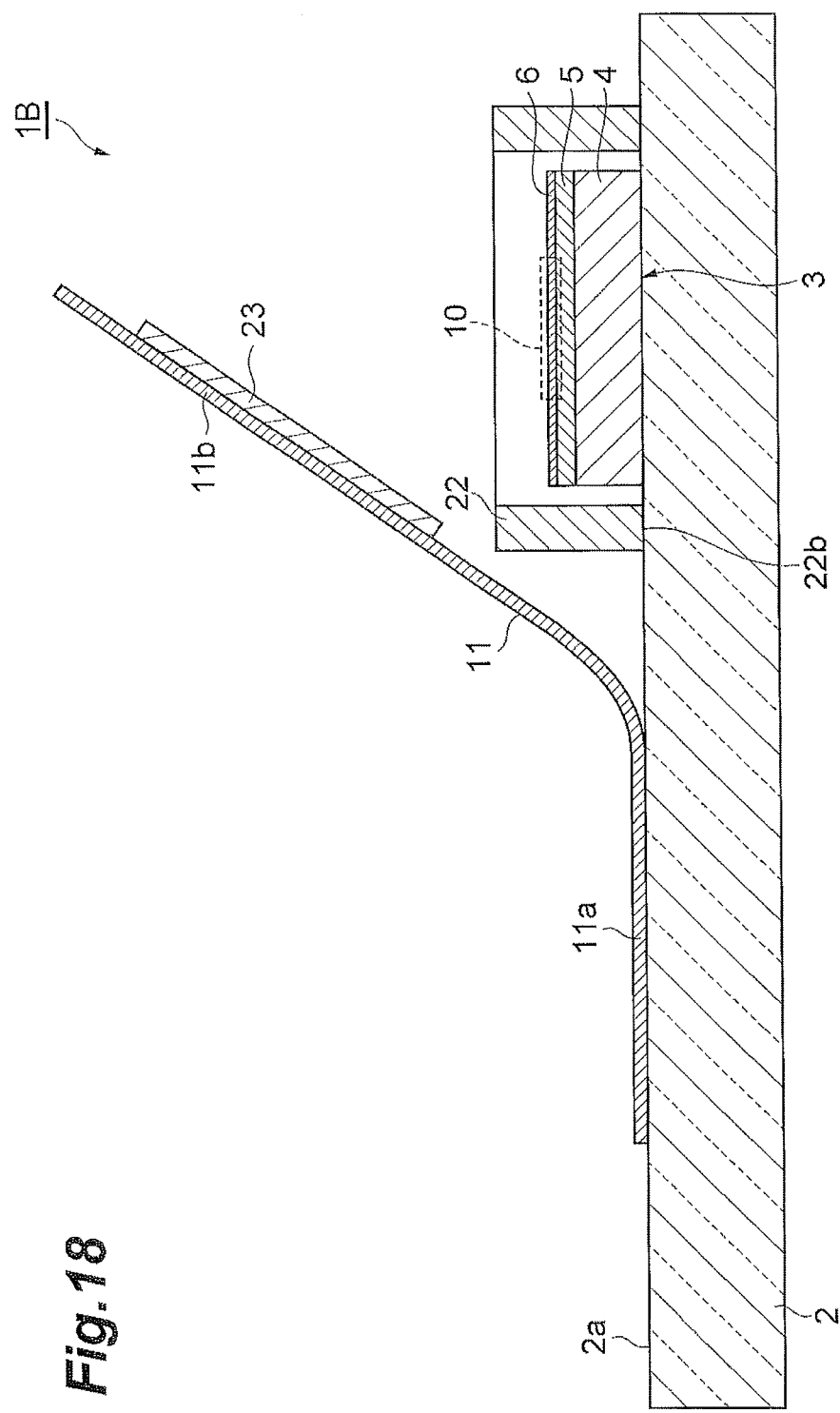
FIG. 18 is a sectional view illustrating a step of using the surface-enhanced Raman scattering unit of FIG. 16.

The opposing part 23 is made thinner than the surrounding part 22, and the weakened part 24 is formed in the boundary part between the surrounding part 22 and opposing part 23 in the SERS unit 1B as well. Therefore, when a part of the leading end part 11b of the seal member 11 is held and lifted, the opposing part 23 having the leading end part 11b of the seal member 11 attached thereto also rises as illustrated in FIG. 18. At this time, the cap 21 breaks at the boundary part between the surrounding part 22 and opposing part 23 from the weakened part 24 serving as a start point, whereby the opposing part 23 having the leading end part 11b of the seal member 11 attached thereto is removed from the surrounding part 22. Thus, the package 20B irreversibly exposes the space S by removing the opposing part 23 from the surrounding part 22.

Thus constructed SERS unit 1B exhibits the following effects in addition to those in common with the above-mentioned SERS unit 1A. That is, since the package 20B is the cap 21 attached onto the handling board 2, the SERS unit 1B can utilize the handling board 2 so as to simplify the structure of the package 20B for containing the optical function part 10 in the space S and configured to irreversibly expose the space S.

Figure 19:
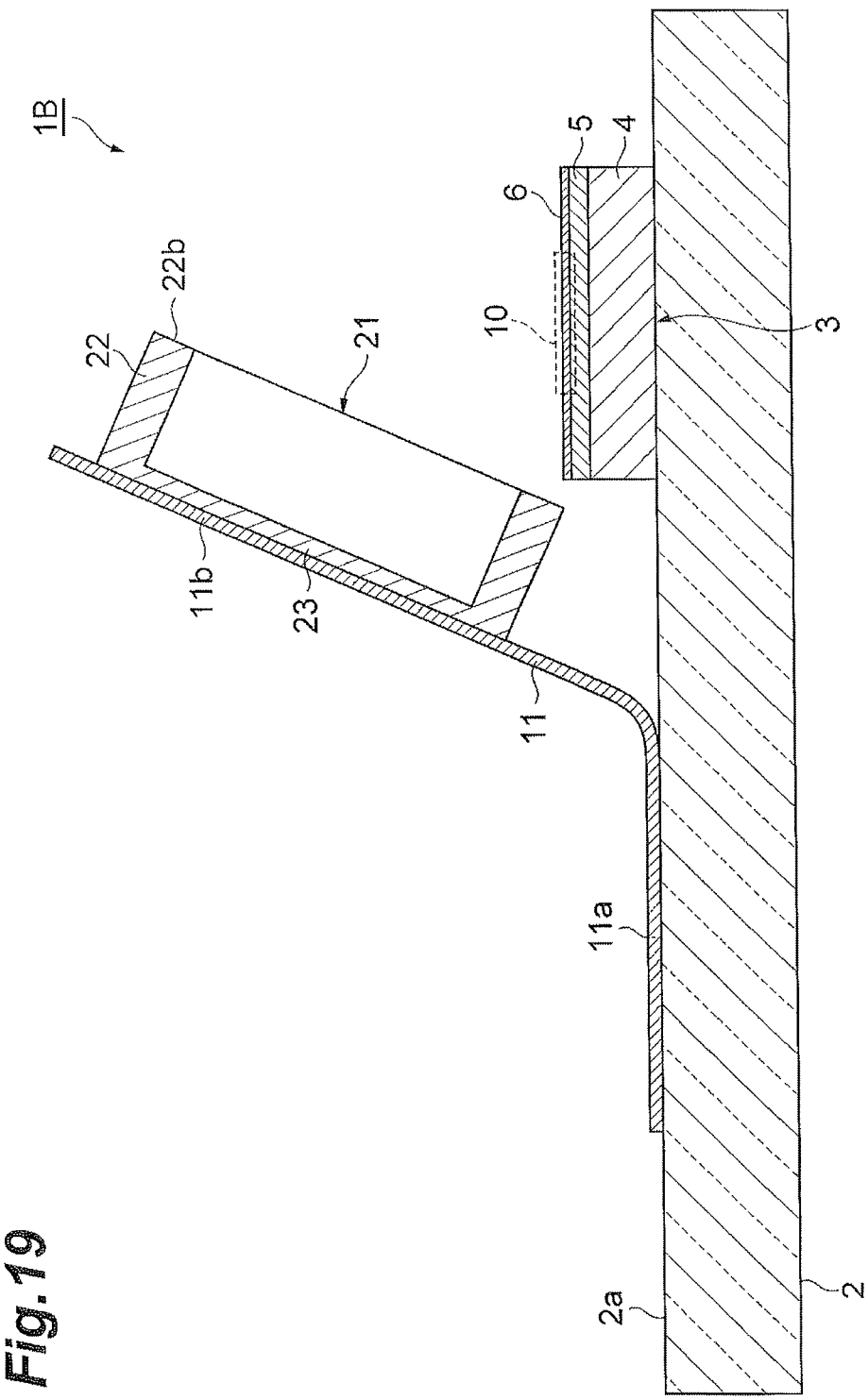
FIG. 19 is a sectional view illustrating a step of using a modified example of the surface-enhanced Raman scattering unit in accordance with the second embodiment of the present invention.

Modified examples of the above-mentioned SERS unit 1B will now be explained. As illustrated in FIG. 19, the cap 21 may be configured to irreversibly expose the space S by being removed as a whole from above the handling board 2. That is, when a part of the leading end part 11b of the seal member 11 is held and lifted when used, the joint between the end face 22b of the surrounding part 22 and the front face 2a of the handling board 2 breaks, whereby the cap 21 as a whole is removed from above the handling board 2. In this case, the weakened part 24 is not formed in the boundary part between the surrounding part 22 and opposing part 23. It is also unnecessary for the opposing part 23 to be made thinner. For arranging the solution sample 12 (or a dispersion of a powder sample in a solution such as water or ethanol) on the optical function part 10, a spacer formed into a shape equivalent to that of the surrounding part 22 by silicone, for example, may be arranged on the handling board 2.

This configuration makes it unnecessary to form the weakened part 24 or thin the opposing part 23 more than necessary in order for the opposing part 23 to be removed easily from the surrounding part 22 when used. Hence, the strength of the cap 21 as a whole can be improved so that the inert space S containing the optical function part 10 can be kept more securely before used.

Figure 20:
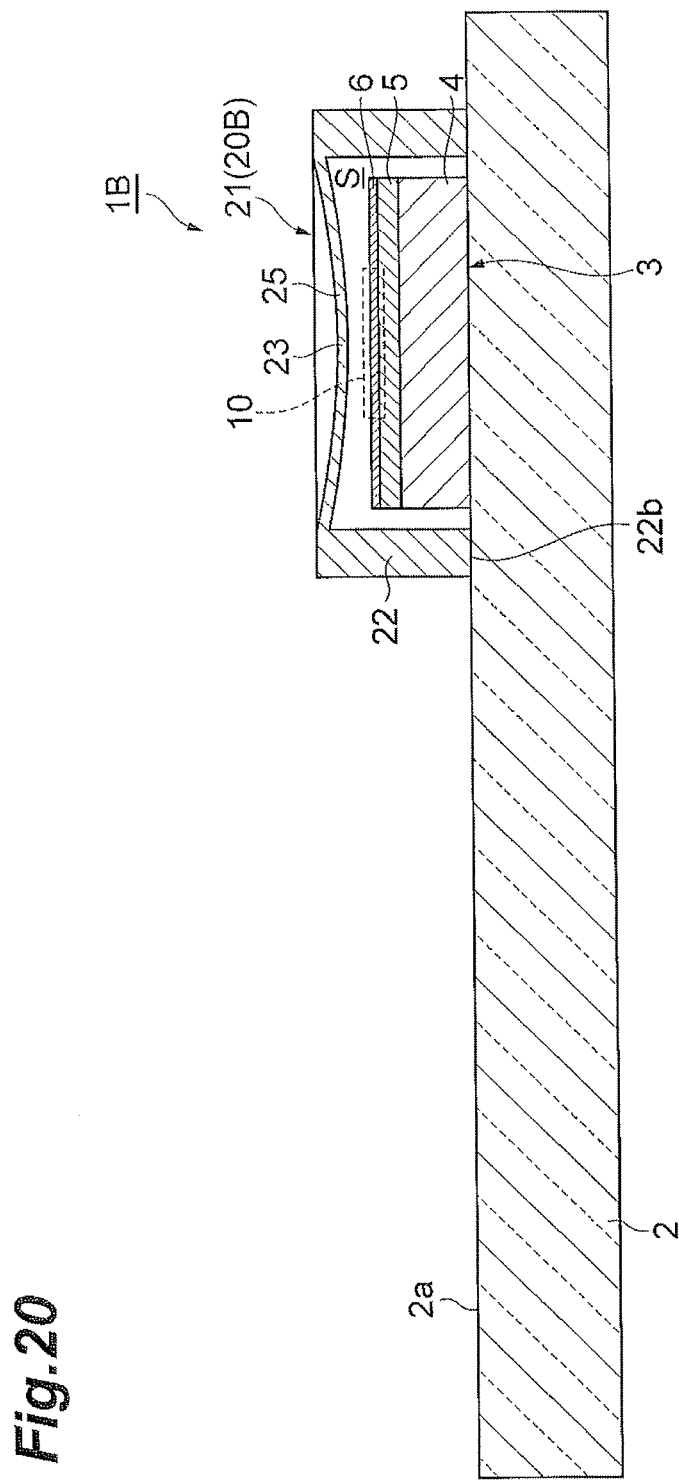
FIG. 20 is a sectional view of a modified example of the surface-enhanced Raman scattering unit in accordance with the second embodiment of the present invention.

As illustrated in FIG. 20, the cap 21 attached onto the handling board 2 may have the deformable part 25 configured to deform according to a difference in pressure between the space S and the outside of the cap 21. Here, the opposing part 23 having a thickness smaller than that of the surrounding part 22 also serves as the deformable part 25 and achieves the inert space S by raising the degree of vacuum, Hence, the deformable part 25 is deformed so as to be depressed. When the inert space S is achieved by filling with an inert gas so as to yield a pressure exceeding the atmospheric pressure, the deformable part 25 deforms so as to inflate. This configuration makes it possible to determine according to the state of deformation of the deformable part 25 whether or not the package 20B is unsealed or whether or not a leak occurs before used.

Figure 21:
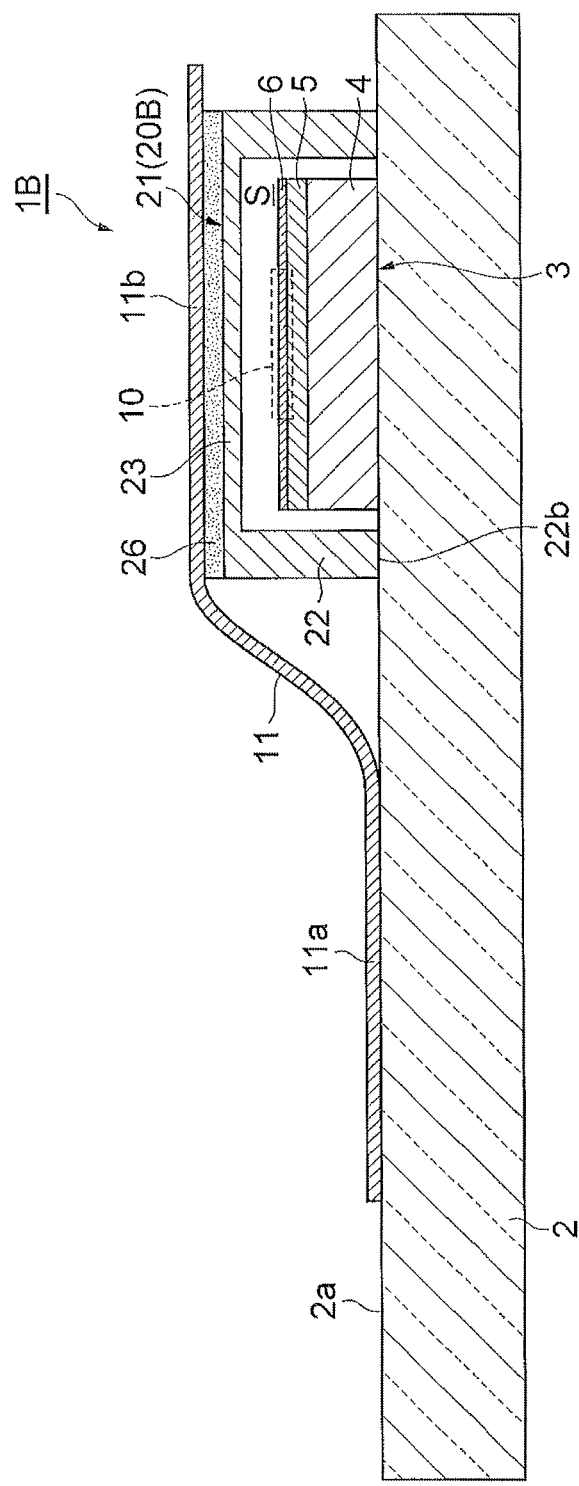
FIG. 21 is a sectional view of a modified example of the surface-enhanced Raman scattering unit in accordance with the second embodiment of the present invention.

As illustrated in FIG. 21, the seal member 11 may be attached to a part of the cap 21 with the resin layer 26 interposed therebetween. Here, the leading end part 11b of the seal member 11 is attached to the opposing part 23 with the resin layer 26 interposed therebetween. This configuration makes it possible to attach the leading end part 11b of the seal member 11 easily and securely to the opposing part 23 even when deflection and the like occur in the opposing part 23.

When a plurality of SERS elements 3 are formed on the handling board 2 in the case where the package 20B is unsealed by removing the opposing part 23 from the surrounding part 22, the surrounding part 22 and opposing part 23 may be provided for each SERS element 3. In this case, the surrounding parts 22 adjacent to each other may be formed either continuously and integrally or separately from each other with a gap therebetween. By attaching the seal member 11 to each opposing part 23 and removing only the opposing part 23 corresponding to the optical function part 10 to be used from the surrounding part 22, this configuration can keep the other optical function parts 10 in the inert spaces S. It can also arrange different samples in the respective optical function parts 10 by removing a plurality of opposing parts 23 from the surrounding parts 22. Thus, a plurality of kinds of samples can be measured on the same handling board 2 without being mixed. It can further save the trouble of replacing the SERS unit 1B and so forth at the time of measurement, thereby improving operational efficiency.

When a plurality of SERS elements 3 are formed on the handling board 2 in the case where the package 20B is unsealed by removing the cap 21 as a whole from above the handling board 2, a plurality of caps 21 may be attached onto the handling board 2 for the respective SERS elements 3. In this case, it is necessary for the surrounding parts 22 adjacent to each other to be formed separately from each other with a gap therebetween. By attaching the seal members 11 to the respective caps 21 and removing only the cap 21 corresponding to the optical function part 10 to be used from above the handling board 2, this configuration can keep the other optical function parts 10 in the inert spaces S. It can also arrange different samples in the respective optical function parts 10 by removing a plurality of caps 21 from above the handling board 2. Thus, a plurality of kinds of samples can be measured on the same handling board 2 without being mixed. It can further save the trouble of replacing the SERS unit 1B and so forth at the time of measurement, thereby improving operational efficiency.

Third Embodiment

Figure 22:
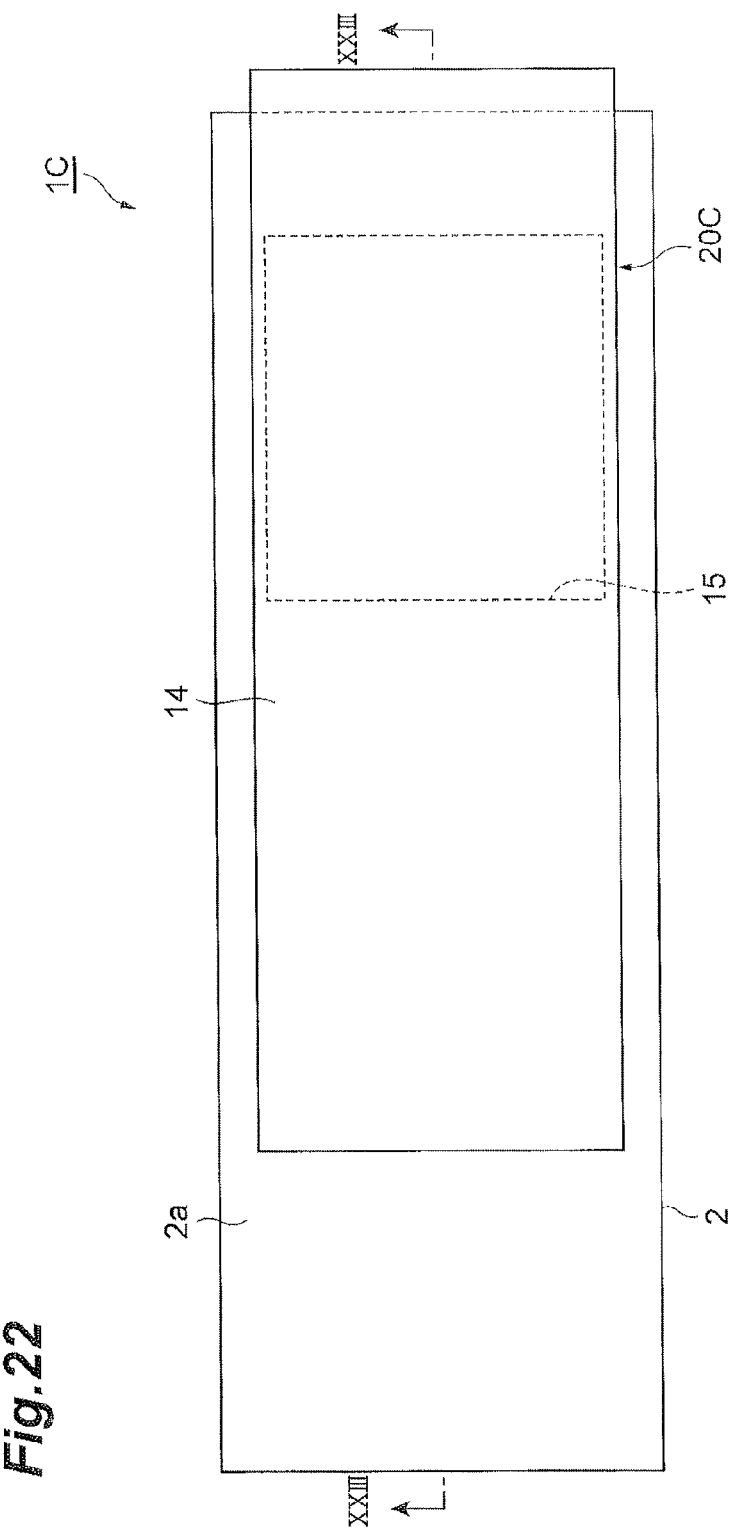
FIG. 22 is a plan view of the surface-enhanced Raman scattering unit in accordance with a third embodiment of the present invention.
Figure 23:
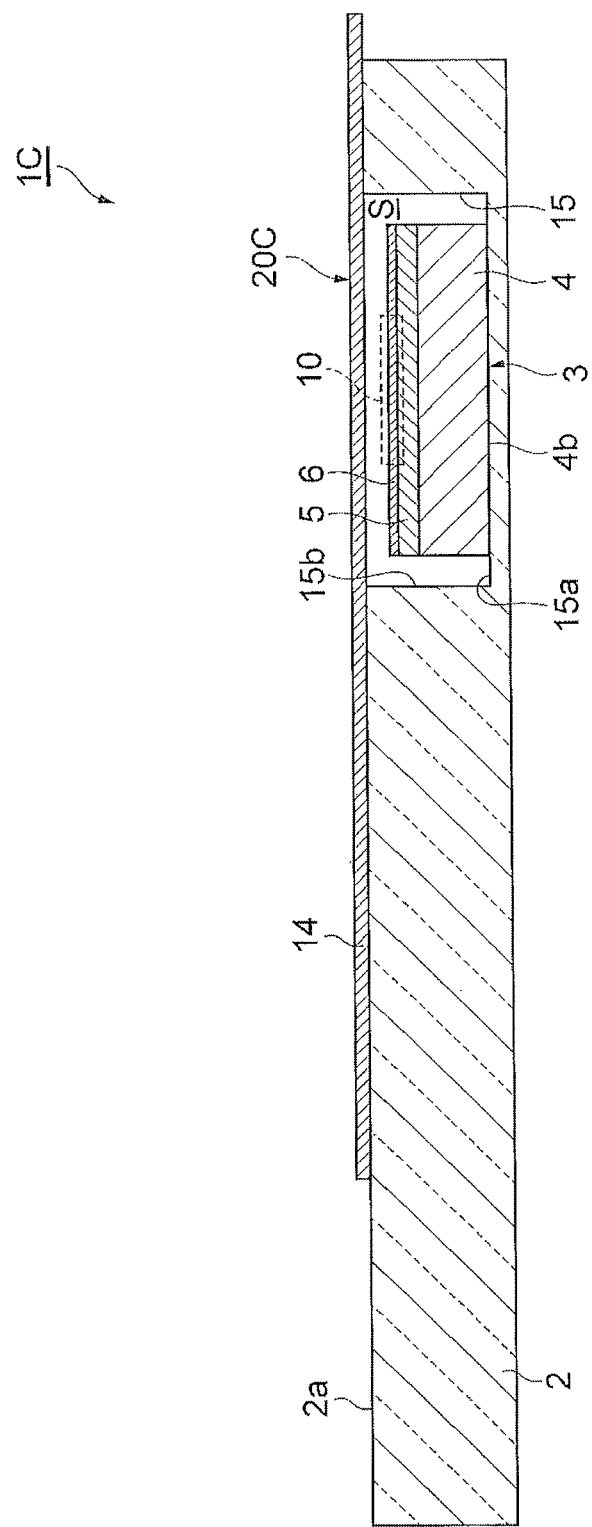
FIG. 23 is a sectional view taken along the line XXIII-XXIII of FIG. 22.
Figure 24:
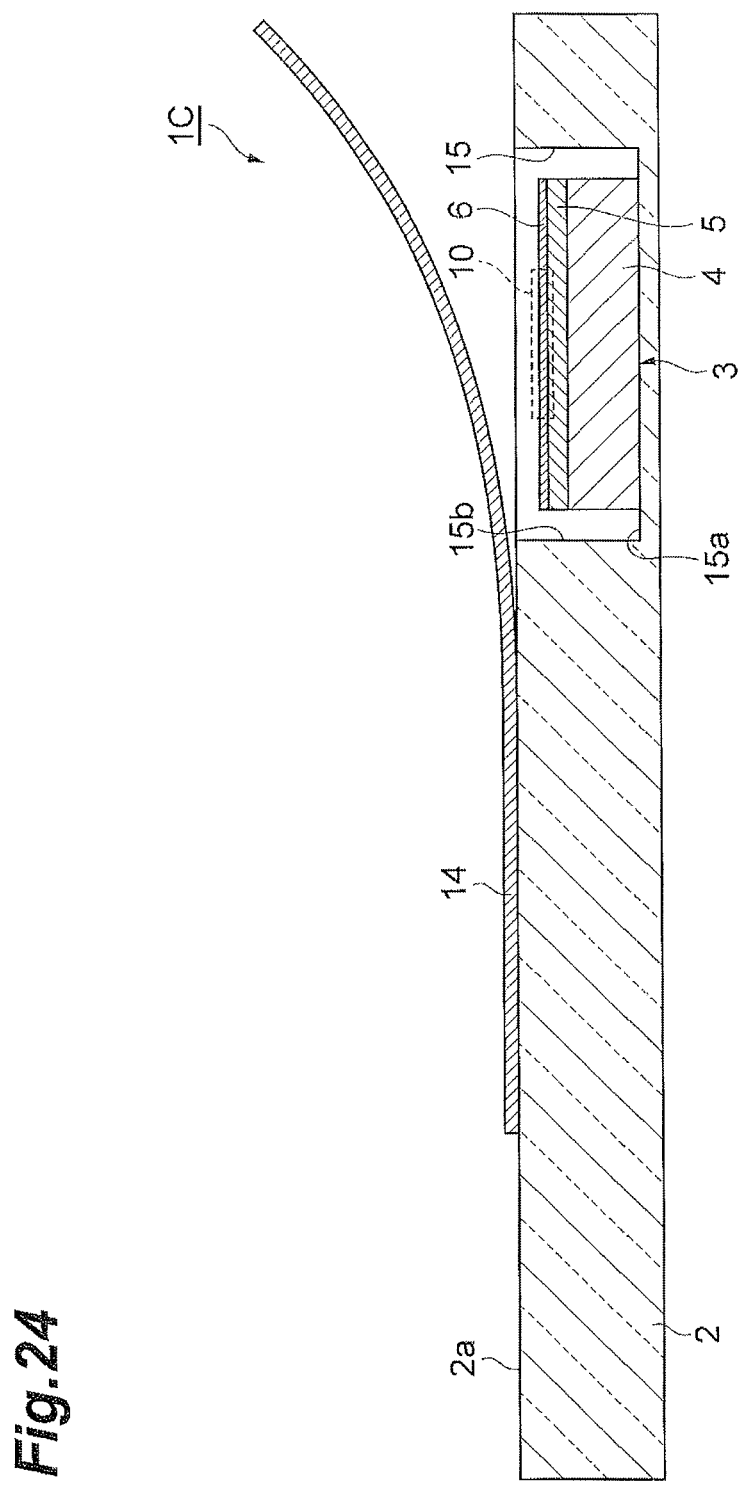
FIG. 24 is a sectional view illustrating a step of using the surface-enhanced Raman scattering unit of FIG. 22.

As illustrated in FIGS. 22 and 23, a SERS unit 1C differs from the above-mentioned SERS unit 1A mainly in that a package 20C is constituted by the handling board 2 and a sheet 14. In the SERS unit 1C, a depression 15 having a rectangular cross section for containing the SERS element 3 is formed on the front face 2a of the handling board 2. Within the depression 15, the rear face 4b of the substrate 4 of the SERS element 3 is secured to a bottom face (inner surface) 15a of the depression 15 by direct bonding, bonding with a metal such as solder, eutectic bonding, fusion bonding by irradiation with laser light and the like, anodic bonding, or bonding with a resin. In this state, an opening 15b of the depression 15 is sealed with the sheet 14 attached to the front face 2a of the handling board 2. In the SERS unit 1C, the package 20C irreversibly exposes the space S by removing the sheet 14 from the handling board 2 as illustrated in FIG.

24. The handling board 2 having the depression 15 may be either a board made of glass, ceramic, silicon, or the like with the depression 15 formed by etching, blasting, or the like or one molded from plastics such as PET, poly carbonate, polypropylene, styrol resin, ABS resin, polyethylene, PMMA, silicone, and liquid crystal polymers, molded glass, or the like.

Thus constructed SERS unit 1C exhibits the following effects in addition to those in common with the above-mentioned SERS unit 1A. That is, by utilizing the handling board 2, the SERS unit 1C can simplify the structure of the package 20C for containing the optical function part 10 in the space S and configured to irreversibly expose the space S. It can also arrange the sample stably on the optical function part 10 by utilizing the depression 15 of the handling board 2.

Fourth Embodiment

Figure 25:
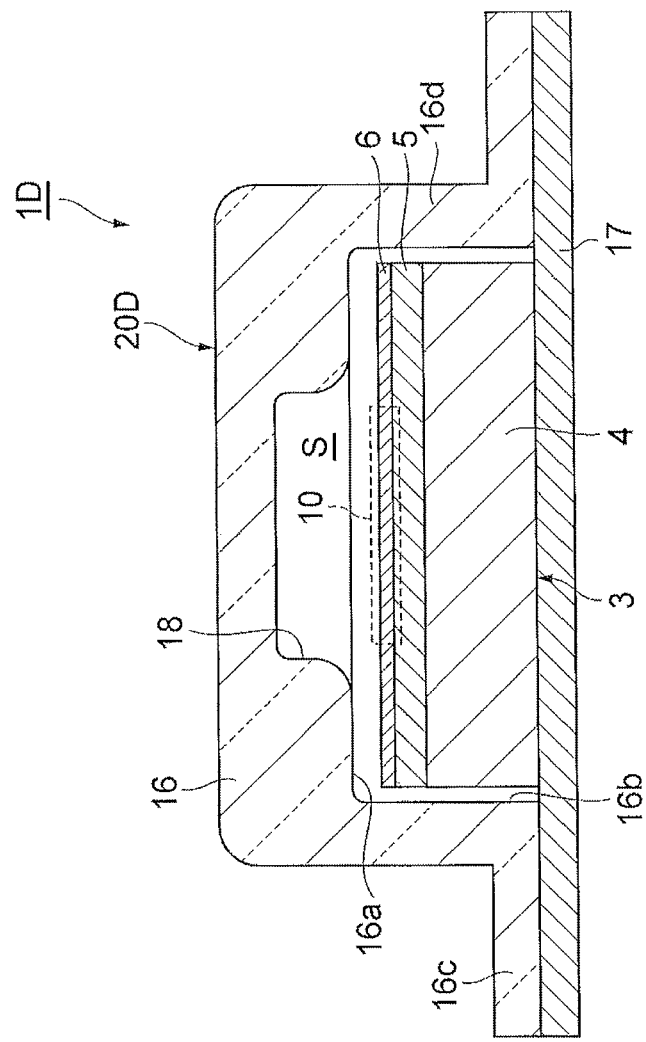
FIG. 25 is a sectional view of the surface-enhanced Raman scattering unit in accordance with a fourth embodiment of the present invention.

As illustrated in FIG. 25, a SERS unit 1D differs from the above-mentioned SERS unit 1A mainly in that a package 20D is constituted by a cap 16 and a sheet 17. In the SERS unit 1D, the SERS element 3 is contained in the cap 16 while the substrate 4 of the SERS element 3 is located on the side opposite from a bottom face (inner surface) 16a of the cap 16. The cap 16 has an opening 16b provided with an outwardly expanding flange part 16c. The opening 16b of the cap 16 is sealed with the sheet 17 bonded to the flange part 16c. Within the cap 16, its side wall part 16d restrains the SERS element 3 from moving in directions parallel to the bottom face 16a of the cap 16. In this state, a recess 18 is formed in the bottom face 16a of the cap 16 so as to oppose the optical function part 10 of the SERS element 3. The cap 16 is integrally formed from a highly moisture-proof plastic such as polypropylene, polyvinyl chloride, or polyolefin. The sheet 17 is an aluminum foil or the like.

In the SERS unit 1D, the cap 16 is deformed by such an external force acting thereon as to collapse it, which causes the substrate 4 to break the sheet 17, whereby the package 20D irreversibly exposes the space S. This allows the SERS element 3 to be taken out. When taking the SERS element 3 out of the package 20D, the bottom face 16a of the cap 16 comes into contact with the conductor layer 6 around the optical function part 10 (i.e., the conductor layer 6 formed on the frame part 9 of the molded layer 5), but the recess 18 serves as a clearance region for the optical function part 10, which keeps the bottom face 16a of the cap 16 from coming into contact with the optical function part 10.

Thus constructed SERS unit 1D exhibits the following effects in addition to those in common with the above-mentioned SERS unit 1A. That is, it can improve the degree of freedom in handling the SERS element 3 having taken out of the package 20D. It can also prevent the cap 16 and the optical function part 10 from interfering with each other when the SERS element 3 is contained or taken out of the package 20D. A plurality of SERS units 1D may be connected into a matrix by joining their flange parts 16c together. Forming weakened parts such as modified parts, cuts, cracks, and grooves in boundary parts of the flange parts 16c adjacent to each other makes it possible to separate a required number of SERS units 1D.

Figure 26:
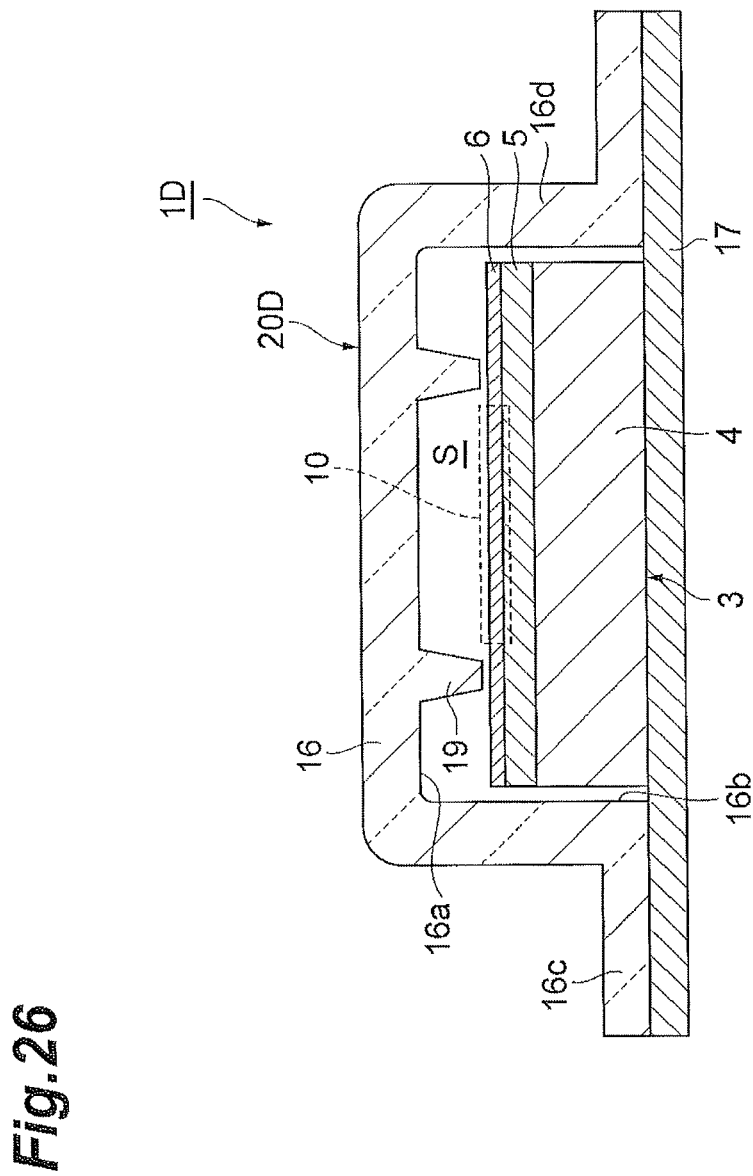
FIG. 26 is a sectional view of a modified example of the surface-enhanced Raman scattering unit in accordance with the fourth embodiment of the present invention.

Modified examples of the above-mentioned SERS unit 1D will now be explained. As illustrated in FIG. 26, a projection 19 may be formed on the bottom face 16a of the cap 16. The projection 19 is formed into a rectangular ring around the optical function part 10 so as to oppose the substrate 4. As a consequence, when taking the SERS element 3 out of the package 20D, the projection 19 comes into contact with the conductor layer 6 around the optical function part 10 (i.e., the conductor layer 6 formed on the frame part 9 of the molded layer 5), but the bottom face 16a of the cap 16 and the projection 19 do not come into contact with the optical function part 10. This can prevent the cap 16 and the optical function part 10 from interfering with each other when the SERS element 3 is contained in or taken out of the package 20D. A plurality of projections 19 may be provided so as to oppose the substrate 4 around the optical function part 10. The projection 19 may be provided so as to be either in contact with or separated from the SERS element 3 in the state where the SERS element 3 contained in the package 20D is in contact with the sheet 17.

Figure 27:
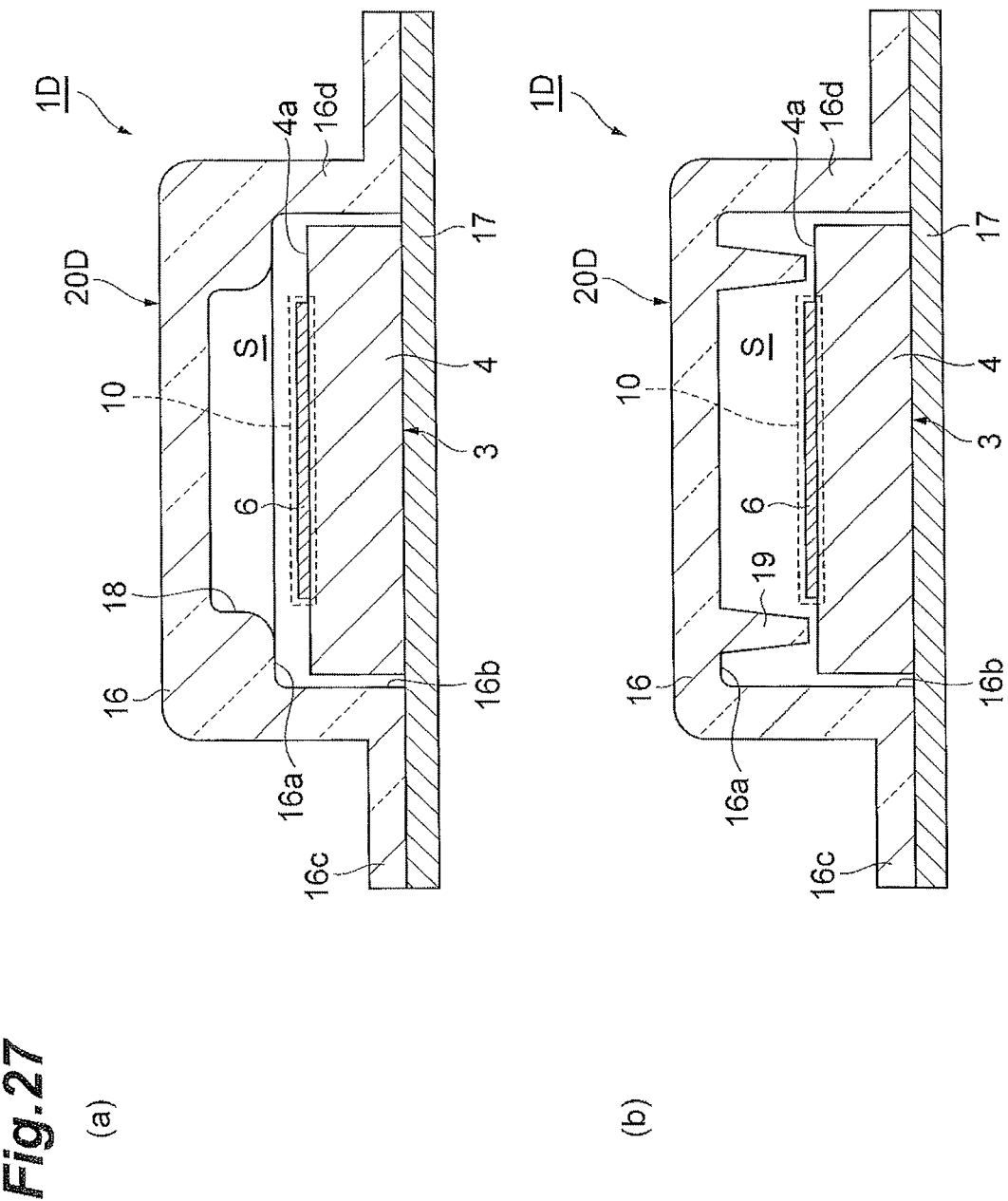
FIG. 27 is a sectional view of a modified example of the surface-enhanced Raman scattering unit in accordance with the fourth embodiment of the present invention.

As illustrated in FIG. 27, when the SERS element 3 is contained in the package 20D or taken out of the package 20D in the case where the SERS element 3 in which the front face 4a of the substrate 4 is exposed in a part other than the optical function part 10 is contained in the package 20D, the bottom face 16a of the cap 16 around the recess 18 may be brought into contact with the exposed front face 4a of the substrate 4 ((a) in FIG. 27) or the projection 19 may be brought into contact with the exposed front face 4a of the substrate 4 ((b) in FIG. 27).

Fifth Embodiment

Figure 33:
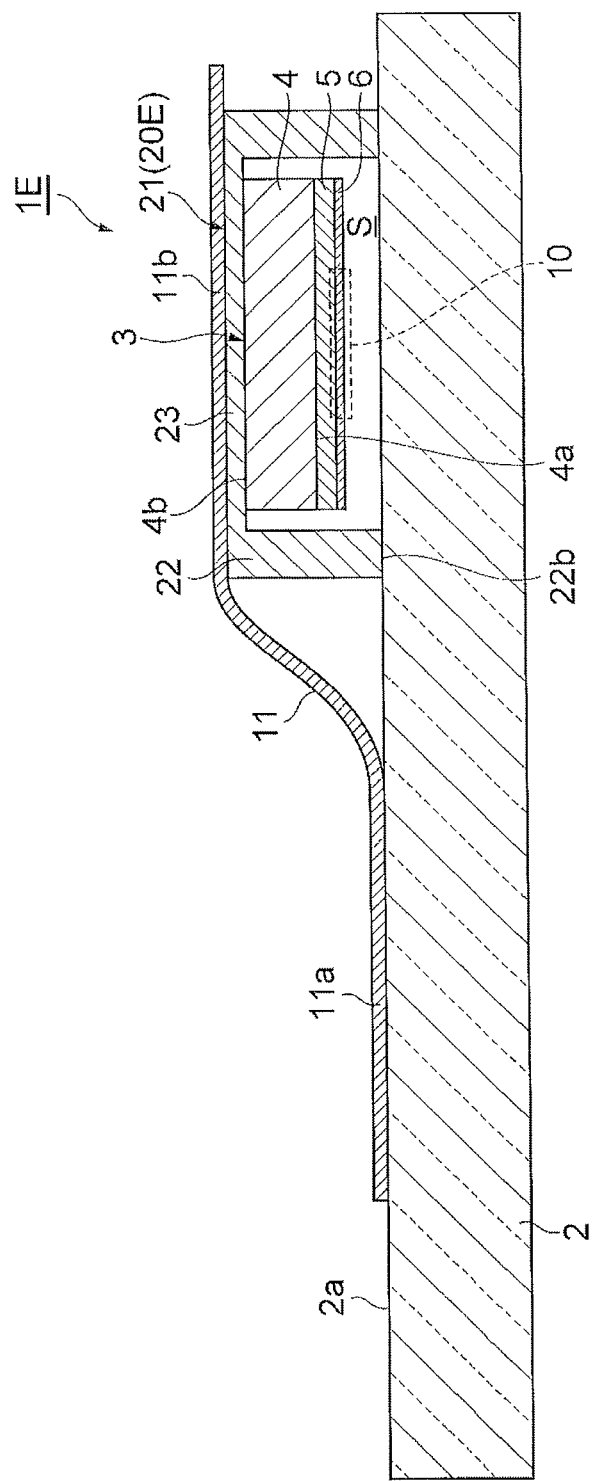
FIG. 33 is a sectional view of the surface-enhanced Raman scattering unit in accordance with a fifth embodiment of the present invention.

As illustrated in FIG. 33, a SERS unit 1E differs from the modified example of the SERS unit 1B illustrated in FIG. 19 mainly in that the SERS element 3 is attached to the cap 21. In the SERS unit 1E, a package 20E for containing the optical function part 10 formed on the substrate 4 in the inert space S is the cap 21 attached onto the handling board 2. The end face 22b of the surrounding part 22 of the cap 21 is secured to the front face 2a of the handling board 2 by direct bonding, bonding with a metal such as solder, eutectic bonding, fusion bonding by irradiation with laser light and the like, anodic bonding, or bonding with a resin.

The substrate 4 of the SERS element 3 is attached to the inner surface of the cap 21 such that the optical function part 10 opposes the front face 2a of the handling board 2. The rear face 4b of the substrate 4 is secured to the inner surface of the opposing part 23 of the cap 21 by direct bonding, bonding with a metal such as solder, eutectic bonding, fusion bonding by irradiation with laser light and the like, anodic bonding, or bonding with a resin.

Figure 34:
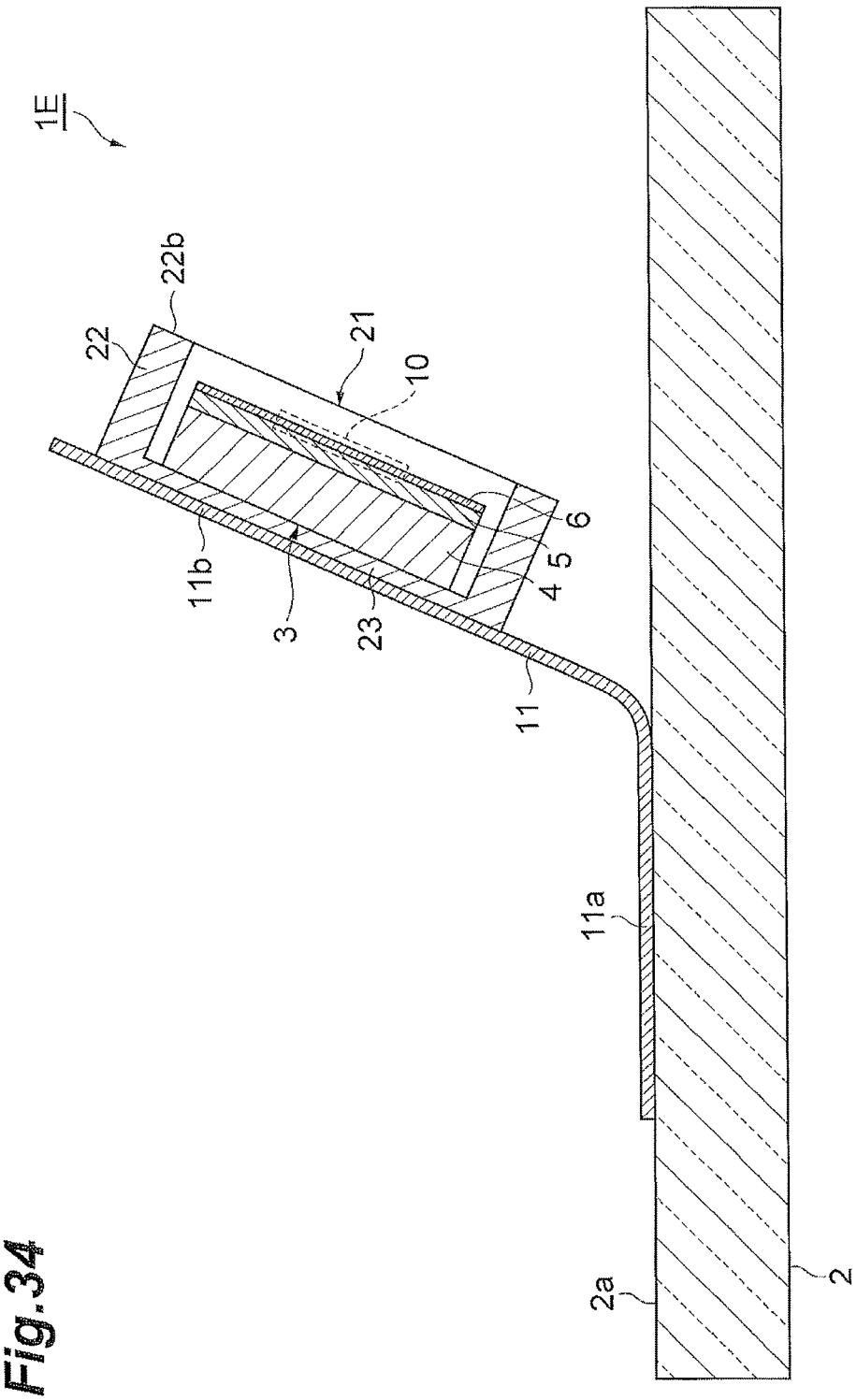
FIG. 34 is a sectional view illustrating a step of using the surface-enhanced Raman scattering unit of FIG. 33.

As illustrated in FIG. 34, the SERS unit 1E is configured such that, when a part of the leading end part 11b of the seal member 11 is held and lifted when used, the joint between the end face 22b of the surrounding part 22 and the front face 2a of the handling board 2 breaks, whereby the cap 21 as a whole is removed from above the handling board 2. Thus, the cap 21 irreversibly exposes the space S by being removed as a whole from above the handling board 2. The seal member 11 may be attached to the cap 21 with the resin layer 26 interposed therebetween.

Thus constructed SERS unit 1E exhibits the following effects in addition to those in common with the modified example of the SERS unit 1B illustrated in FIG. 19. That is, the SERS unit 1E can inhibit foreign matters and impurities from adhering to the optical function part 10 when removing the cap 21 as a whole from above the handling board 2.

A plurality of caps 21 may be attached onto the handling board 2, the substrate 4 of the SERS element 3 being attached to the inner surface of the cap 21 for each cap 21. By unsealing only the cap 21 containing the optical function part 10 to be used, this configuration can keep the optical function parts 10 contained in the other caps 21 in the inert spaces S. It also becomes possible to measure a plurality of kinds of samples in the respective caps 21 without mixing them. It can further save the trouble of replacing the SERS unit 1B and so forth at the time of measurement, thereby improving operational efficiency.

While the first to fifth embodiments of the present invention are explained in the foregoing, the present invention is not limited to the above-mentioned embodiments. For example, the space S may have various forms such as cylindrical, conical, and quadrangular prism forms in addition to the truncated quadrangular pyramid form. The SERS units 1A to 1E may have such a structure that a plurality of optical function parts 10 are contained in the same packages 20A to 20E, e.g., one (the same) opposing part 23 corresponds to a plurality of optical function parts 10 in the first and second embodiments. As in the foregoing, without being restricted to those mentioned above, various materials and forms can be employed for the constituents of the SERS units 1A to 1E.

The fine structure part 7 may be formed on the front face 4a of the substrate 4 either indirectly, for example, with the support part 8 interposed therebetween, or directly. The conductor layer 6 is not limited to the one directly formed on the fine structure part 7, but may be formed indirectly on the fine structure part 7 with a layer such as a buffer metal (Ti, Cr, or the like) for improving the adhesion of a metal to the fine structure part 7, for example, interposed therebetween.

Figure 28:
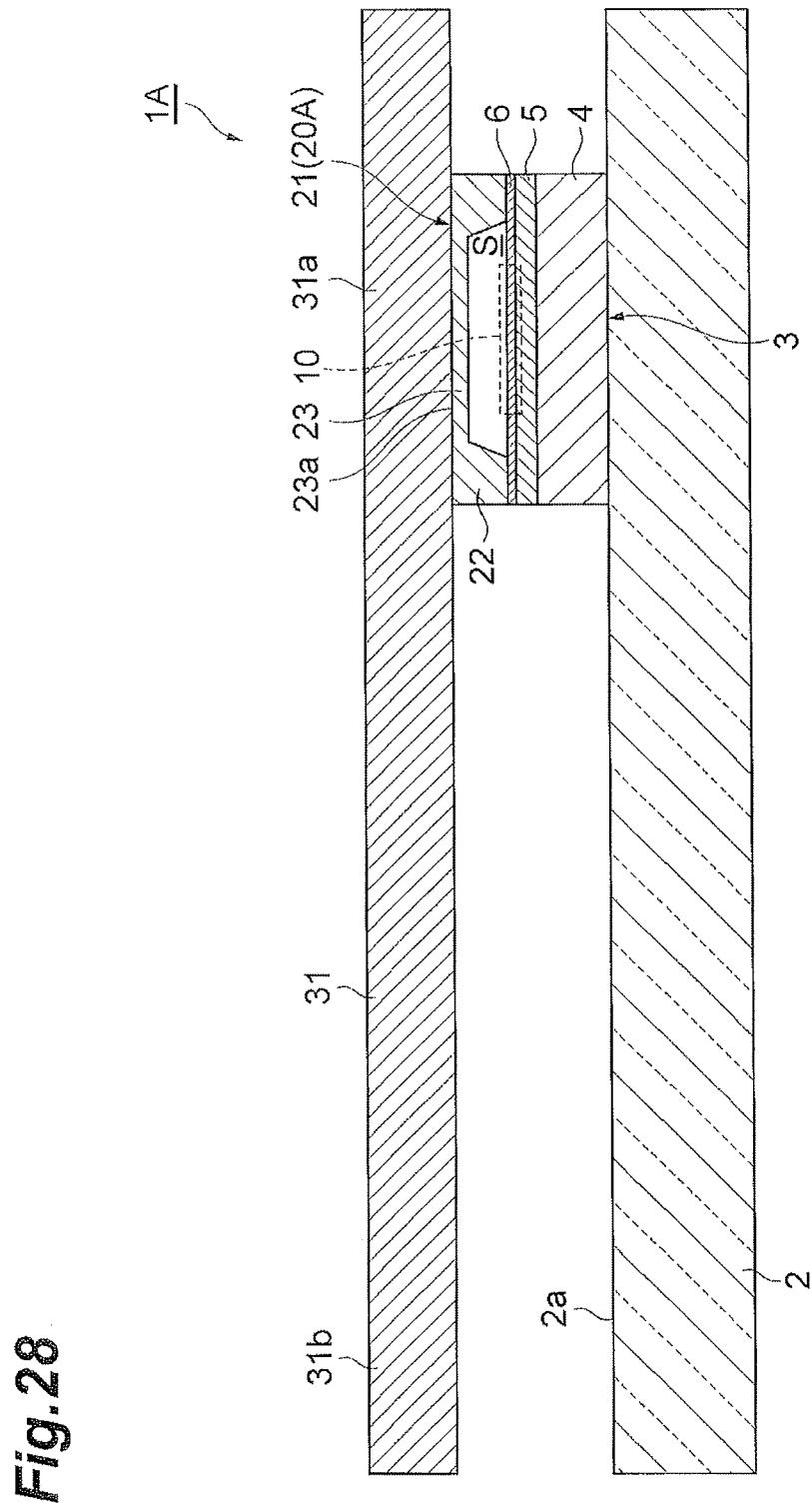
FIG. 28 is a sectional view of a modified example of the surface-enhanced Raman scattering unit in accordance with the first embodiment of the present invention.

As illustrated in FIG. 28, a rigid member (holding member) 31 may be attached to the cap 21 in place of the seal member 11 in the SERS unit 1A of the first embodiment. The rigid member 31 is formed into a rectangular plate by a resin, a metal, a ceramic, glass, or the like. The rigid member 31 has a base end part 31a secured to the surface 23a of the opposing part 23 of the cap 21 by direct bonding, bonding with a metal such as solder, eutectic bonding, fusion bonding by irradiation with laser light and the like, anodic bonding, or bonding with a resin and a leading end part 31b which is a free end. In this case, the leading end part 31b of the rigid member 31 is moved toward and away from the handling board 2, so as to remove the opposing part 23 of the cap 21 or the whole cap 21 together with the rigid member 31. The cap 21 may integrally be formed with the rigid member 31. In the SERS unit 1B of the second embodiment, the rigid member 31 may be attached to the cap 21 in place of the seal member 11.

Figure 29:
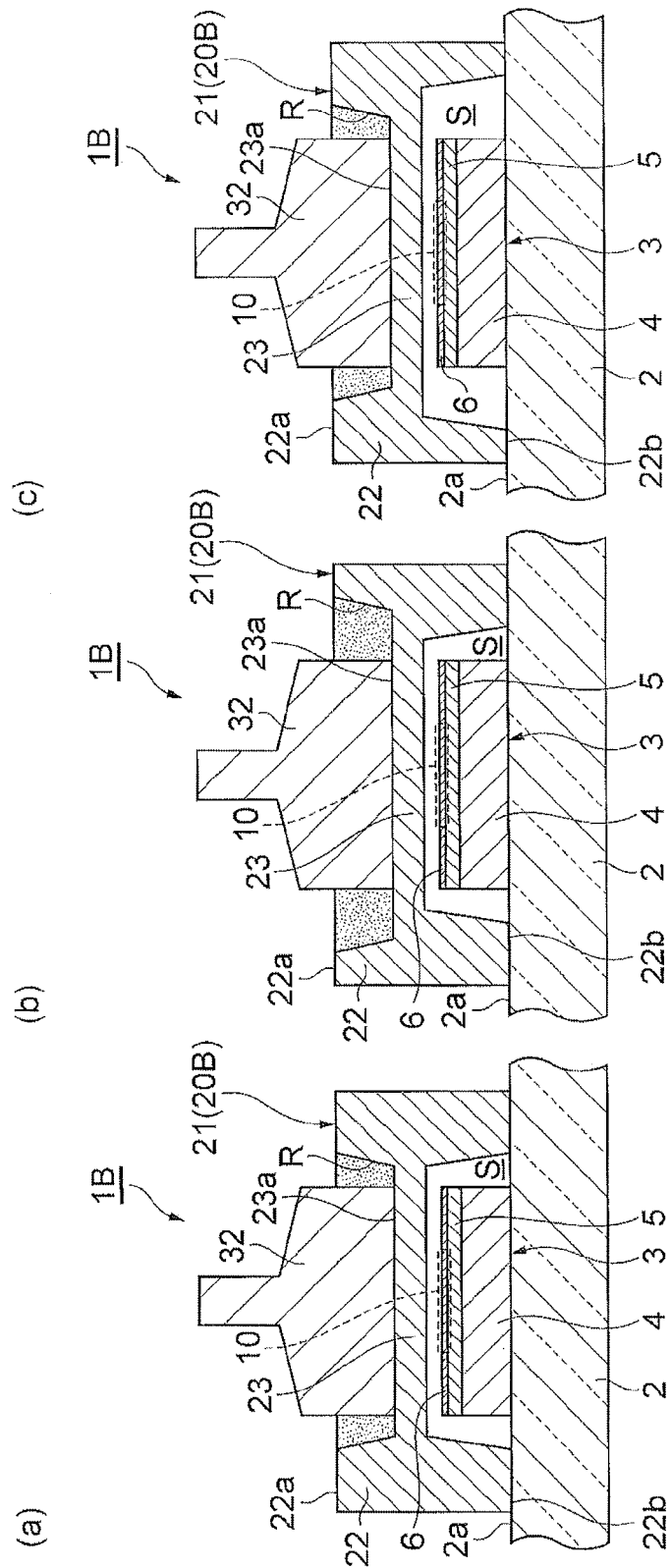
FIG. 29 is a sectional view of a modified example of the surface-enhanced Raman scattering unit in accordance with the second embodiment of the present invention.

As illustrated in FIG. 29, a projecting member (holding member) 32 may be attached to the cap 21 in place of the seal member 11 in the SERS unit 1B of the second embodiment. The projecting member 32 is made of a resin, a metal, a ceramic, glass, or the like and secured to the surface 23a of the opposing part 23 of the cap 21 by direct bonding, bonding with a metal such as solder, eutectic bonding, fusion bonding by irradiation with laser light and the like, anodic bonding, or bonding with a resin. When the end face 22a of the surrounding part 22 of the cap 21 projects to the opposite side of the handling board 2 from the surface 23a of the opposing part 23 in the case of joining with a metal such as solder or a resin, a region R surrounded by the surrounding part 22 on the surface 23a of the opposing part 23 reserves the metal such as solder or resin, so as to secure the projecting member 32 to the surface 23a of the opposing part 23 easily and securely. In this case, the projecting member 32 is held and lifted, so as to remove the opposing part 23 of the cap 21 together with the projecting member 32.

Figure 30:
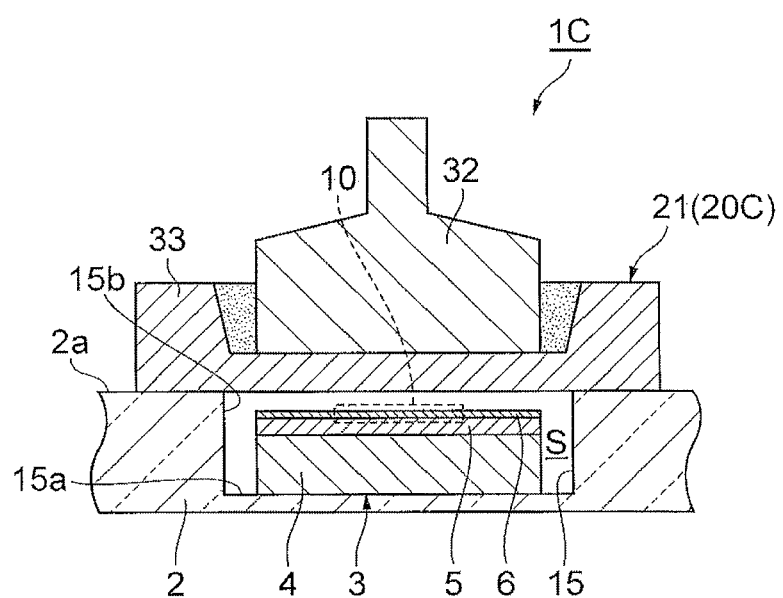
FIG. 30 is a sectional view of a modified example of the surface-enhanced Raman scattering unit in accordance with the third embodiment of the present invention.
Figure 31:
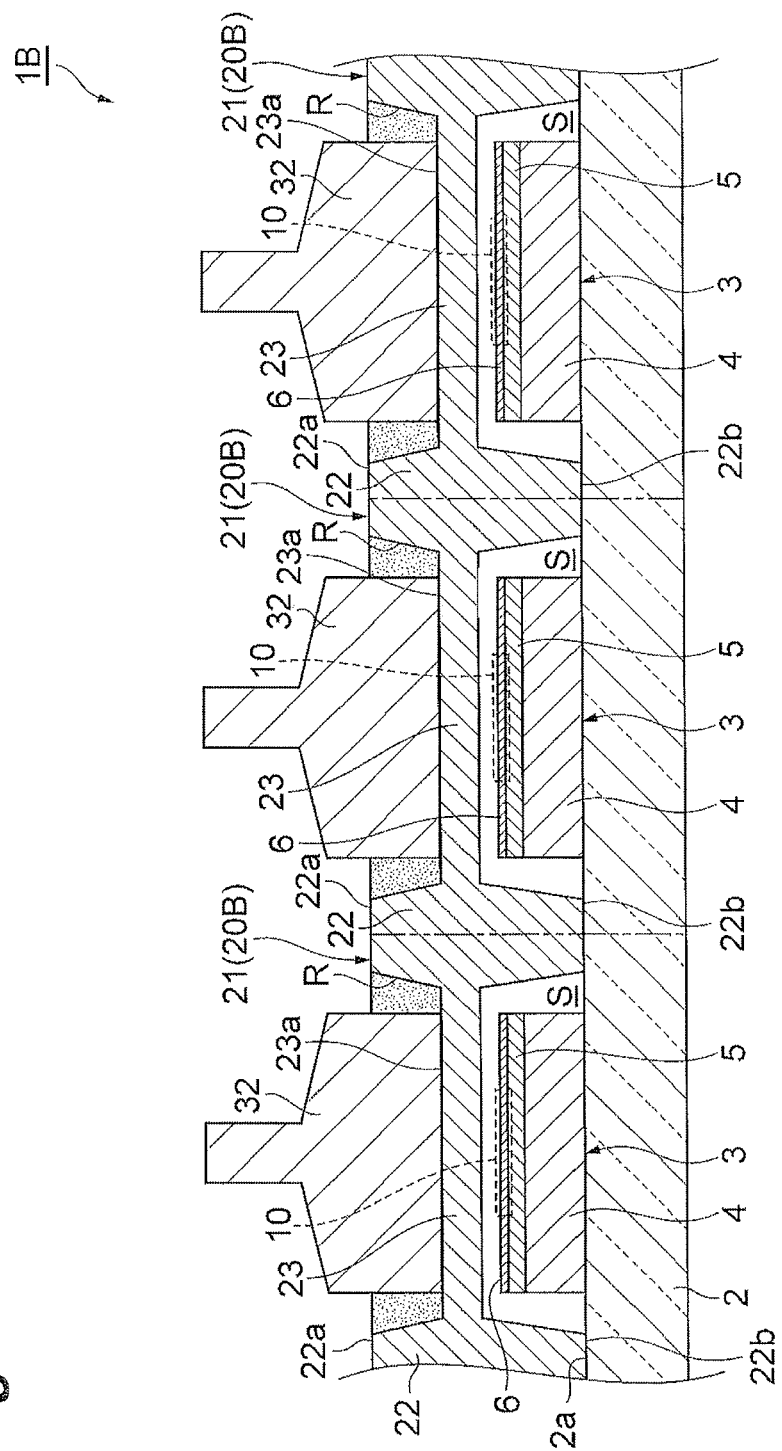
FIG. 31 is a sectional view of a modified example of the surface-enhanced Raman scattering unit in accordance with the second embodiment of the present invention.

When seen in the thickness direction of the substrate 4, the area of the region R may be either on a par with ((a) in FIG. 29), greater than ((b) in FIG. 29), or smaller than ((c) in FIG. 29) that of the space S. The cap 21 may integrally be formed with the projecting member 32. In the SERS unit 1A of the first embodiment, the projecting member 32 may be attached to the cap 21 in place of the seal member 11. As illustrated in FIG. 30, the SERS unit 1C of the third embodiment may be configured such that a cover 33 made of a resin, a metal, a ceramic, glass, or the like seals the opening 15b of the depression 15 in place of the sheet 14, while the projecting member 32 is attached to the cover 33. As illustrated in FIG. 31, when a plurality of SERS units 3 are formed on the handling board 2, the surrounding part 22 and opposing part 23 being provided for each SERS element 3, in the SERS unit 1B of the second embodiment, the projecting member 32 may be attached to each opposing part 23.

As illustrated in FIG. 32, the cap 21 may integrally be formed with a lug part 33 instead of the seal member 11 in the SERS unit 1B of the second embodiment. In this case, tweezers or the like are employed so as to pick up and lift the lug part 33, thereby removing the cap 21 as a whole. The lug part 33 may be formed into a flange ((a) in FIG. 32) or one or a plurality of projections ((b) in FIG. 32). In the SERS unit 1A of the first embodiment, the cap 21 may integrally be formed with the lug 33 instead of the seal member 11.

Figure 35:
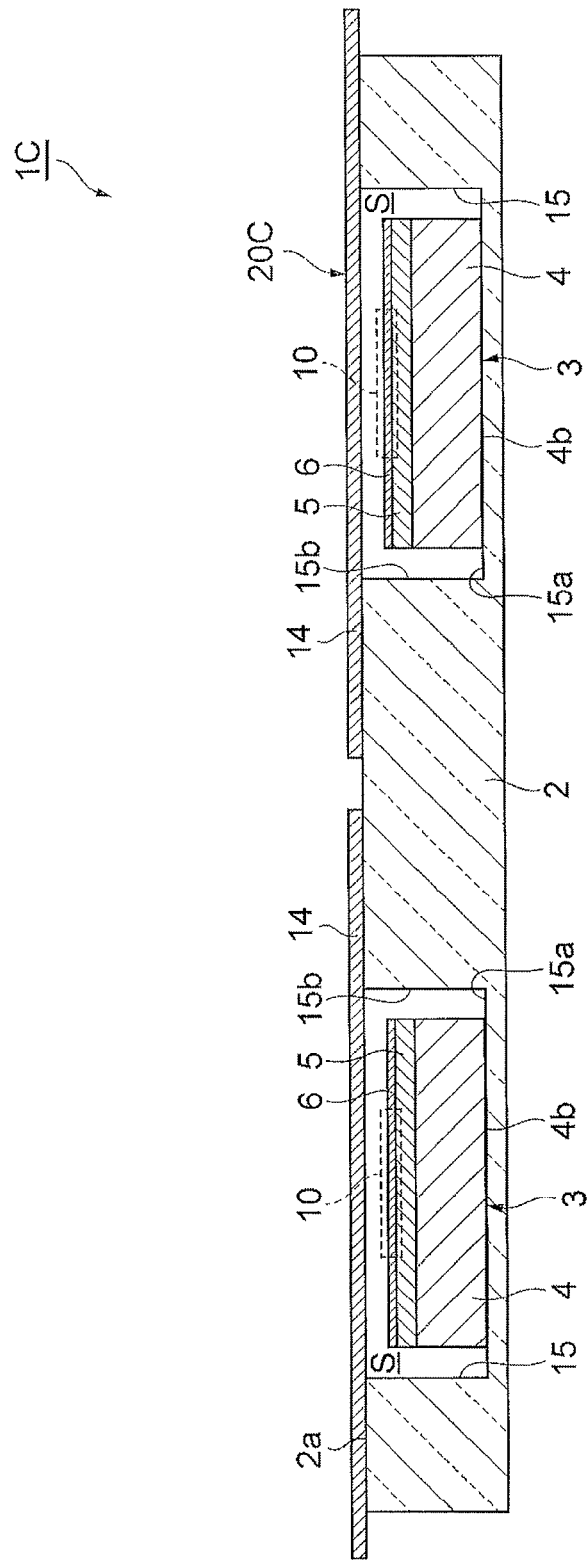
FIG. 35 is a sectional view of a modified example of the surface-enhanced Raman scattering unit in accordance with the third embodiment of the present invention.

As illustrated in FIG. 35, in the SERS unit 1C of the third embodiment, the handling board 2 may have a plurality of depressions 15 each containing the substrate 2 and optical fiber 10 and including an inner surface having the substrate 2 attached thereto. By unsealing only the depression 15 containing the optical function part 10 to be used, this configuration can keep the optical function parts 10 contained in the other depressions 15 in the inert spaces S. It also becomes possible to measure a plurality of kinds of samples on the same handling board 2 without mixing them. It can further save the trouble of replacing the SERS unit 1C and so forth at the time of measurement, thereby improving operational efficiency.

In the SERS unit 1C, a plurality of sheets 14 may be provided for the respective depressions 15. By removing the sheet 14 from the handling board 2 for only the depression 15 containing the optical function part 10 to be used, this configuration can easily and securely unseal this depression 15 and seal the other depressions 15.

As illustrated in FIG. 37, the rear face 2b of the handling board 2 in the SERS unit 1C of the third embodiment may be provided with a plurality of hollow parts 43 so as to form wall parts 41, 42 extending in directions perpendicular to the thickness direction of the handling board 2. Here, the wall part 41 is formed into a ring along the outer edges of the handling board 2, while the wall part 42 is formed like a grid on the inside of the wall part 41. By way of example, each hollow part 43 is formed into a rectangular parallelepiped.

This configuration prevents the handling board 2 from warping, whereby the focal point of excitation light can accurately be placed in the optical function part 10 when arranging the handling board 2 on a stage of a Raman spectroscopic analyzer. In particular, while a material such as a resin which makes it easier to form the depression 15 is selected as a material for the handling board 2 when forming the depression 15 in the handling board 2, such a material is more likely to warp, for which it is very effective to provide the hollow parts 43 as mentioned above. However, the handling board 2 in any of the above-mentioned modes can be provided with the above-mentioned hollow parts 43 in order to prevent it from warping.

On the front face 2a of the handling board 2, a ring-shaped cutout 44 is formed along the outer edges of the handling board 2. The cutout 44 is formed such that the wall part 41 of another SERS unit 1C is arranged therein, whereby a plurality of SERS units 1C can be stacked at the time of transfer and the like.

In the SERS unit 1C illustrated in FIG. 37, the sheet 14 is also lifted to the side opposite from the depression 15 by holding an end part 14a thereof, so as to be removed from the handling board 2. This can irreversibly expose the space S within the package 20C while securely preventing the optical function part 10 from being damaged. Thus, in the sheet 14, its end part 14a is not bonded to the front face 2a of the handling board 2 and therefore functions as a holding part when removing the sheet 14 from the handling board 2.

INDUSTRIAL APPLICABILITY

The present invention can provide a surface-enhanced Raman scattering unit which can prevent its surface-enhanced Raman scattering effect from deteriorating before used and a method for using the same.

REFERENCE SIGNS LIST 1A, 1B, 1C, 1D, 1E: SERS unit (surface-enhanced Raman scattering unit); 2: handling board; 4: substrate; 10: optical function part; 11: seal member (holding member); 14: sheet, 15: depression; 15a: bottom face (inner, surface); 15b: opening; 16: cap; 16a: bottom face (inner surface); 16b: opening; 17: sheet; 18: recess; 19: projection; 20A, 20B, 20C, 20D, 20E: package; 21: cap; 22: surrounding part; 23: opposing part; 24: weakened part; 25: deformable part; 26: resin layer; 31: rigid member (holding member); 32: projecting member (holding member).

The invention claimed is:

1. A surface-enhanced Raman scattering unit comprising:
a substrate;
an optical function part formed on the substrate, for generating surface-enhanced Raman scattering; and
a package containing the optical function part in an inert space and configured to irreversibly expose the space wherein the package has a handling board having a depression containing the substrate and the optical function part, the depression including an inner surface having the substrate attached thereto, and a sheet sealing an opening of the depression; and
wherein the package is configured to irreversibly expose the space when the sheet is removed from the handling board.

2. A surface-enhanced Raman scattering unit according to claim 1, wherein the package is configured to irreversibly expose the space in order to arrange a sample on the optical function part.

3. A surface-enhanced Raman scattering unit according to claim 1, wherein the sheet is lifted to the side opposite from the depression so that the sheet is removed from the handling board.

4. A surface-enhanced Raman scattering unit according to claim 3, wherein an end part of the sheet is held and lifted to the side opposite from the depression so that the sheet is removed from the handling board.

5. A surface-enhanced Raman scattering unit according to claim 1, wherein the handling board has a plurality of such depressions, each of the depressions containing the substrate and the optical function part, and including an inner surface having the substrate attached thereto.

6. A surface-enhanced Raman scattering unit according to claim 5, wherein a plurality of such sheets are provided for the respective depressions.

7. A method for using a surface-enhanced Raman scattering unit comprising:
a substrate;
an optical function part formed on the substrate, for generating surface-enhanced Raman scattering; and
a package containing the optical function part in an inert space and configured to irreversibly expose the space;
the method comprising:
a first step of irreversibly exposing the space by unsealing the package;
a second step of arranging the sample on the optical function part after the first step; and
a third step of irradiating the sample with excitation light after the second step.

* * * * *